US010758581B2

(12) United States Patent
Fares et al.

(10) Patent No.: US 10,758,581 B2
(45) Date of Patent: Sep. 1, 2020

(54) TREATMENT OF CANCER

(71) Applicant: Carmel Haifa University Economic Corporation Ltd., Haifa (IL)

(72) Inventors: Fuad Fares, Hurfeish (IL); Rinat Bar Shalom, Kfar Bialik (IL); Shlomo Grossman, Petah Tikvah (IL); Margalit Bergman, Tel Aviv (IL)

(73) Assignee: CARMEL HAIFA UNIVERSITY ECONOMIC CORPORATION LTD., Haifa (IL)

( * ) Notice: Subject to any disclaimer, the term of this patent is extended or adjusted under 35 U.S.C. 154(b) by 665 days.

(21) Appl. No.: 14/897,505

(22) PCT Filed: Jun. 10, 2014

(86) PCT No.: PCT/IL2014/050525
§ 371 (c)(1),
(2) Date: Dec. 10, 2015

(87) PCT Pub. No.: WO2014/199379
PCT Pub. Date: Dec. 18, 2014

(65) Prior Publication Data
US 2016/0106792 A1   Apr. 21, 2016

Related U.S. Application Data

(60) Provisional application No. 61/833,463, filed on Jun. 11, 2013.

(51) Int. Cl.
*A61K 36/28* (2006.01)
*A61K 36/00* (2006.01)

(52) U.S. Cl.
CPC .................................. *A61K 36/28* (2013.01)

(58) Field of Classification Search
None
See application file for complete search history.

(56) References Cited

FOREIGN PATENT DOCUMENTS

| KR | 20110118748 | * | 9/2011 |
| KR | 20110118748 A | | 9/2011 |
| WO | 0241908 A1 | | 5/2002 |
| WO | WO0241908 | * | 5/2002 |

OTHER PUBLICATIONS

Rozenbiat et al. ("Induction of G2/M arrest and apoptosis Inducing Effects of Compounds Isolated from Inula viscosa" Biochemical Pharmacology, Jan. 2008, 15;75(2):369-82).*
Ershler ("capecitabine monotherapy: safe and effective treatment for metatistic breast cancer" Onocologist 2008, pp. 325-335).*
Rozenbiat et al. ("Induction of G2/M arrest and apoptosis inducing Effects of Compounds Isolated from Inula viscosa" Biochemical Pharmacology, Jan. 2008, 15;75(2);369-82 (Year: 2008).*
Ershler ("Capecitabine montherapy; safe and effective treatment for metatistic breast cancer". Onocologist 2008, pp. 325-335) (Year: 2008).*
"Capecitabine monotherapy: safe and effective treatment for metatistic breast cancer", Ershler WB., Oncologist 2006; 325-35.
"Antiproliferative, Antimicrobial and Apoptosis Inducing Effects of Compounds Isolated from Inula Viscosa", Wamidh Talib et al., Molecules 2012, 17, 3291-3303, Mar. 14, 2012.
"Cytotoxic effect of some Moroccan medicinal plant extracts on human cervical cell lines", Nawal Merghoub et al., Journal of Medicinal Plants Research vol. 3(12), pp. 1045-1050, Dec. 2009.
"Antiproliferative Activity of Plant Extracts Used Against Cancer in Traditional Medicine", Wamidh H. Talibh et al., Scientia Pharmaceutica 2010; 78; 33-45, Feb. 13, 2010.
"Induction of G2/M arrest and apoptosis by sesquiterpene lactones in human melanoma cell lines" Rozenblat et al., Biochemical Pharmacology, Jan. 2008, 15;75(2):369-82.
"Inula Viscosa Extracts Induces Telemere Shortening and Apoptosis in Cancer Cells and Overcome Drug Resistance", Merghoub et al., Nutrition and Cancer Jan. 15, 2016, 1-13.
International Search Report of corresponding PCT Application No. PCT/IL2014/050525.
Lamiae Belayachi et al: "Screening of North African Medicinal Plant Extracts for Cytotoxic Activity Against Tumor Cell Lines", European Journal of Medicinal Plants, vol. 3, No. 3, Apr. 27, 2013 (Apr. 27, 2013), pp. 310-332, XP055326843 (24 pages).
Galya Abrham et al: Inhibition of Inflammatory Cytokine Secretion by Plant-Derived Compounds Inuviscolide and Tomentosin: The Role of and STAT1 the Open Pharmacology Journal, Aug. 19, 2010 (Aug. 19, 2010), pp. 36-44, XP055326833 (9 pages).

* cited by examiner

*Primary Examiner* — Michael Barker
(74) *Attorney, Agent, or Firm* — Roach, Brown, McCarthy & Gruber, P.C.; Kevin D. McCarthy

(57) ABSTRACT

Methods of treating colorectal cancer using water extracts derived from *dittrichia viscosa* leaves are provided.

14 Claims, 54 Drawing Sheets

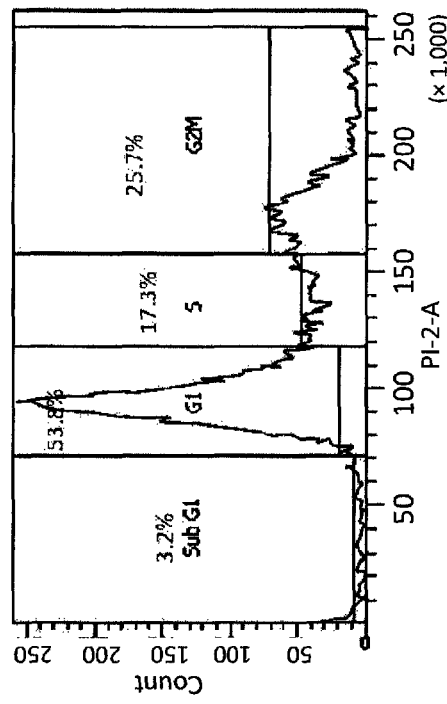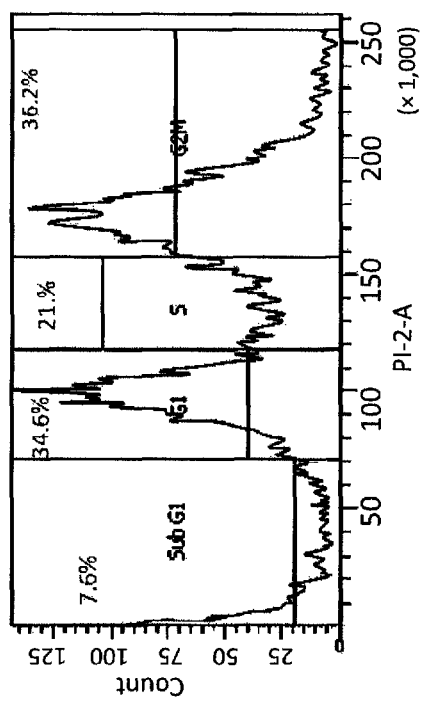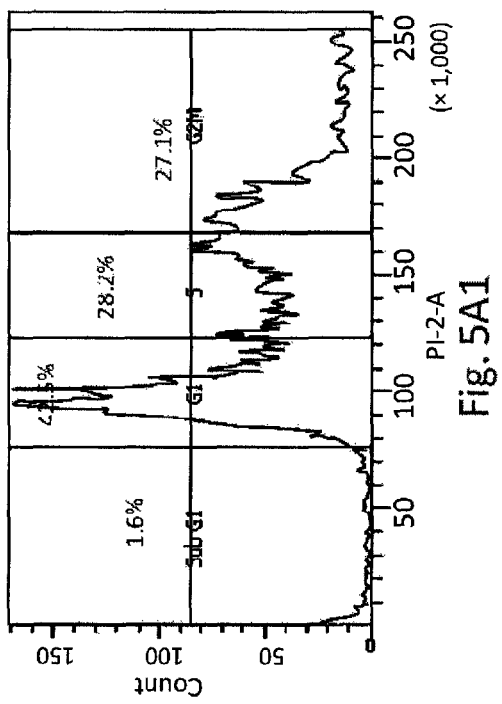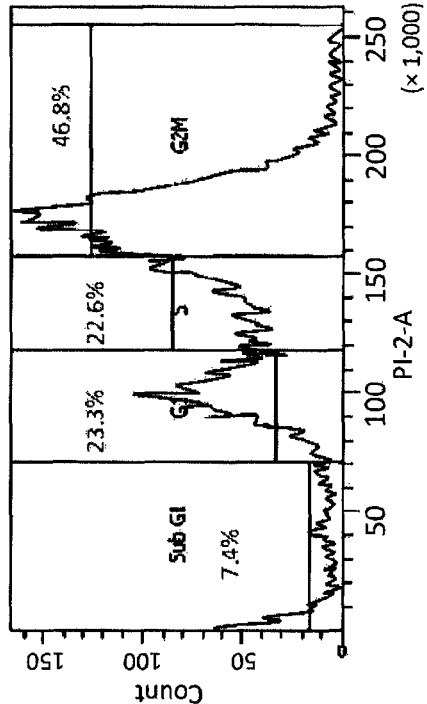
Fig. 5A1  Fig. 5A2  Fig. 5B1  Fig. 5B2

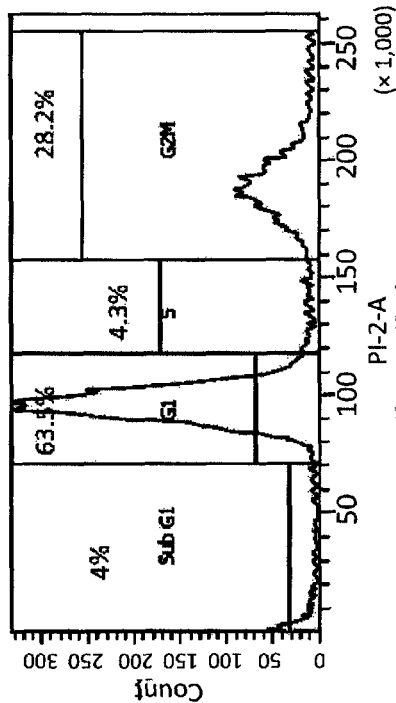
Fig. 5D1
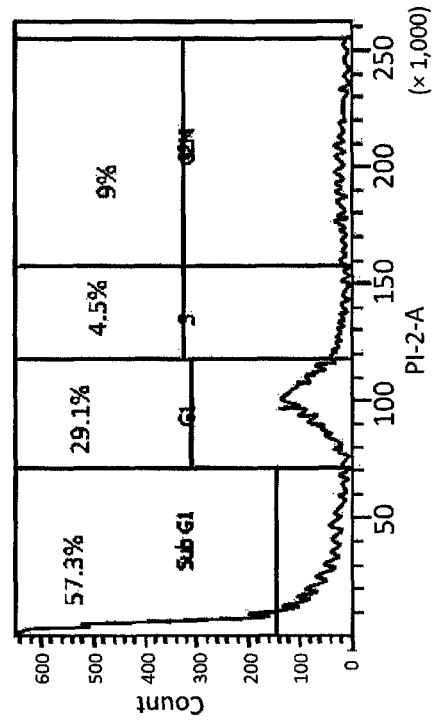
Fig. 5D2
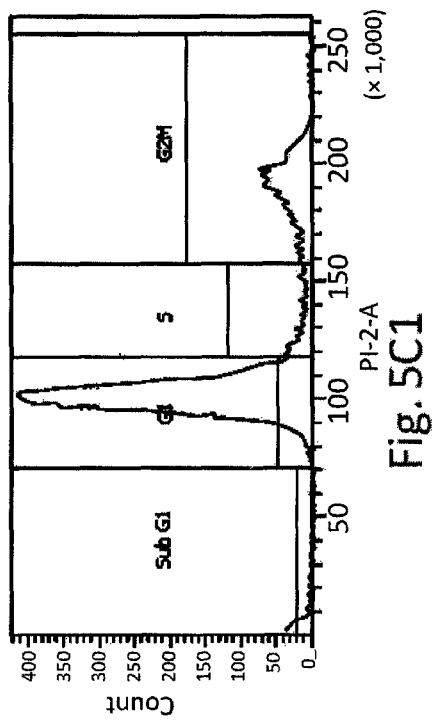
Fig. 5C1
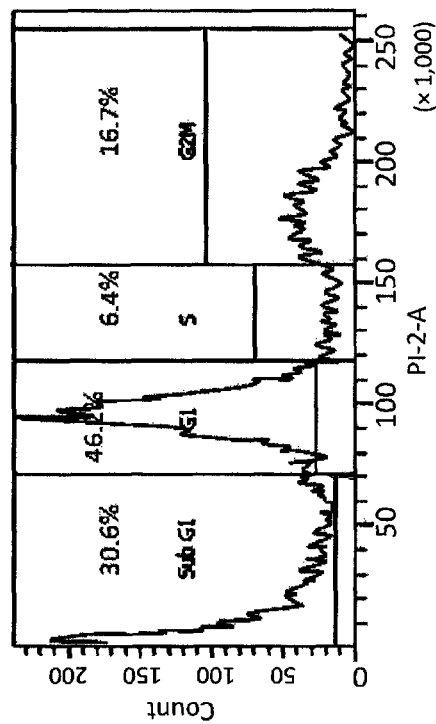
Fig. 5C2

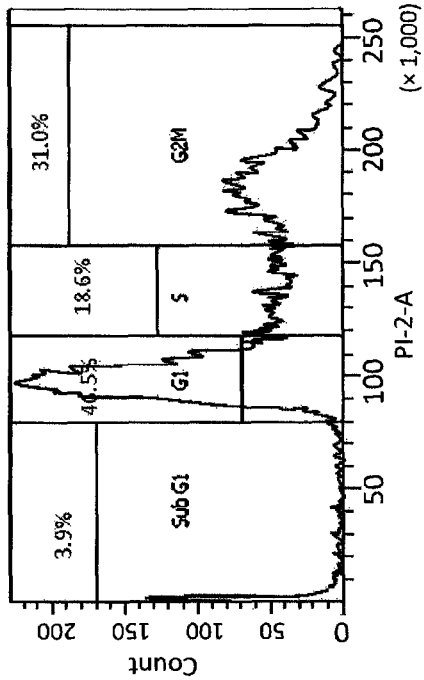
Fig. 7A1
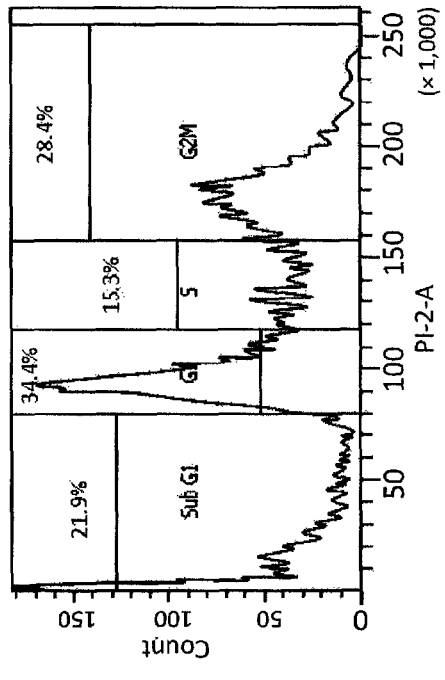
Fig. 7A2
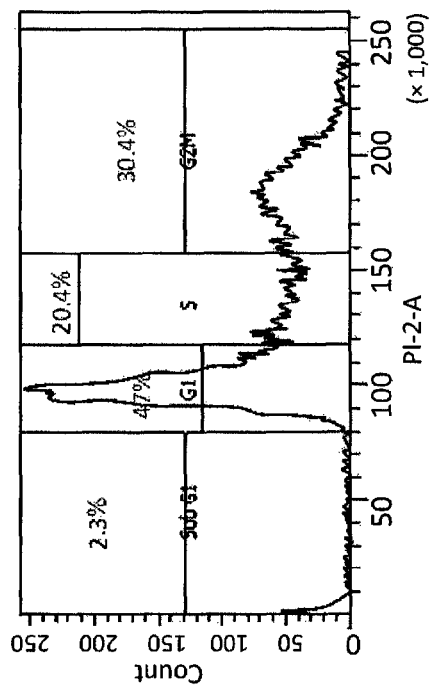
Fig. 7B1
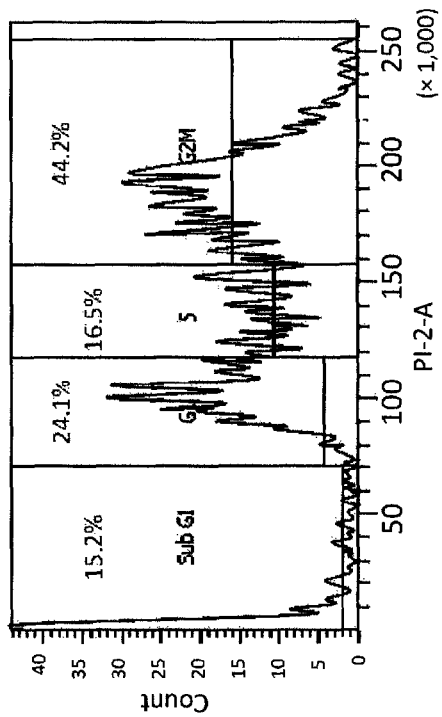
Fig. 7B2

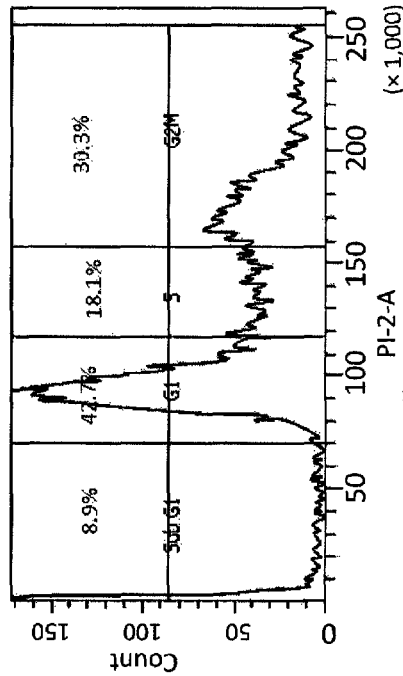
Fig. 7C1
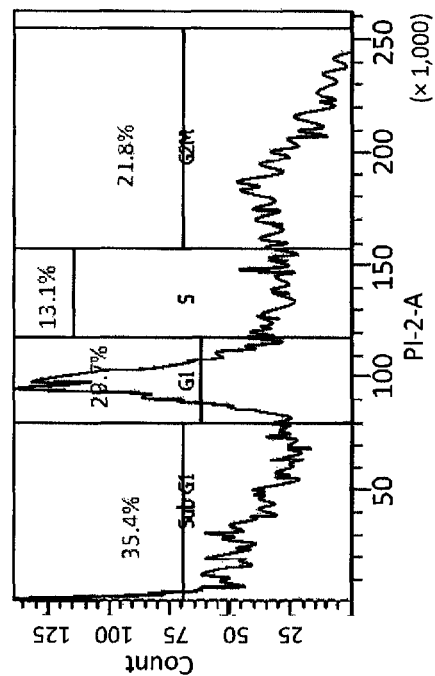
Fig. 7D1
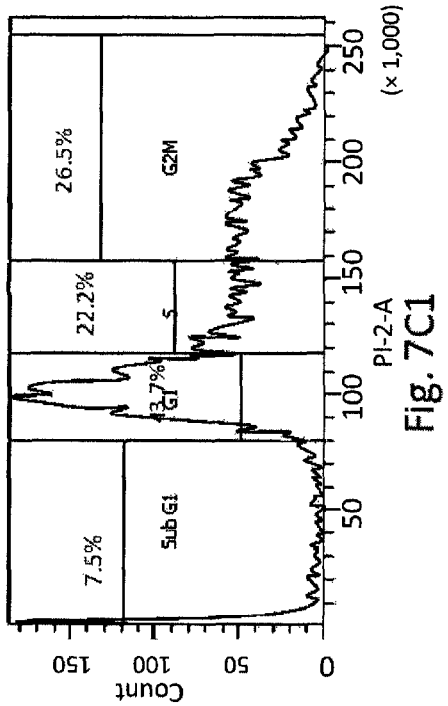
Fig. 7C2
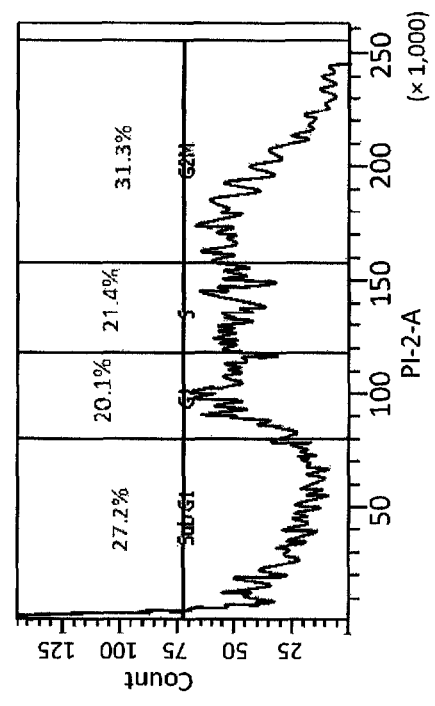
Fig. 7D2

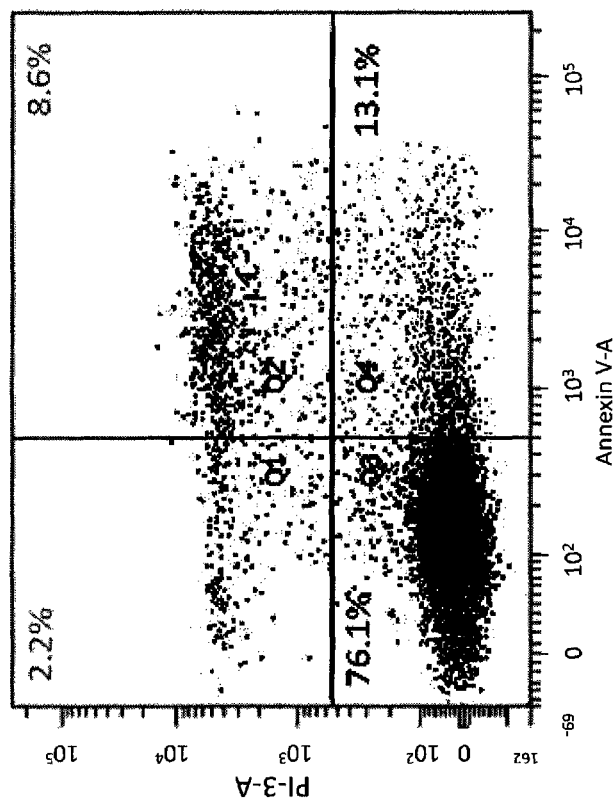

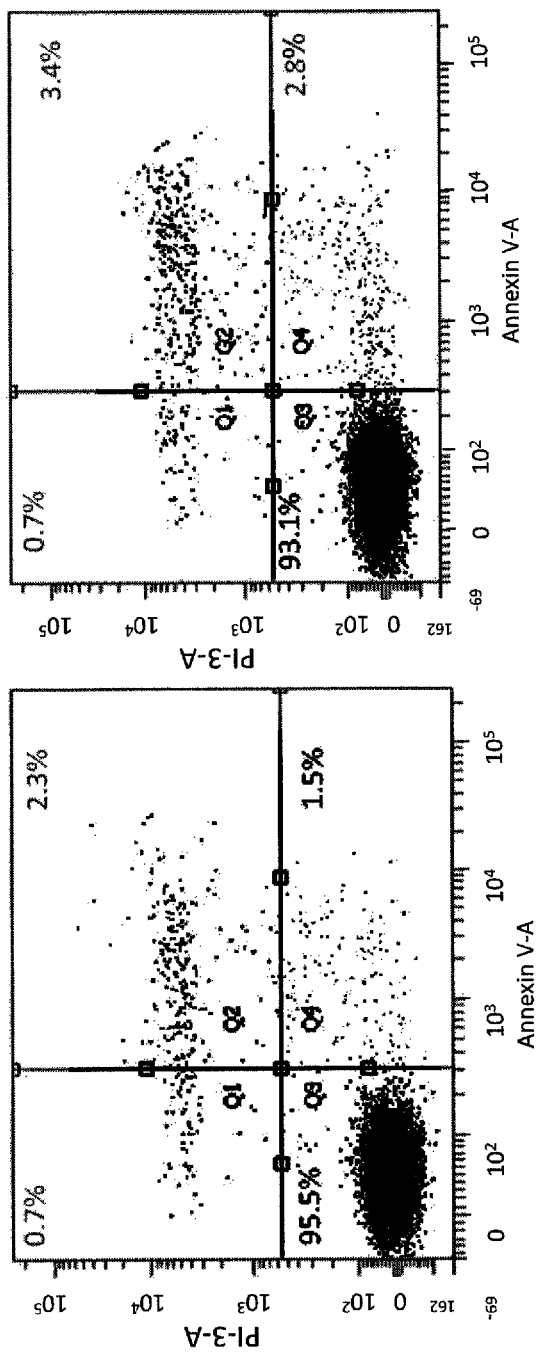

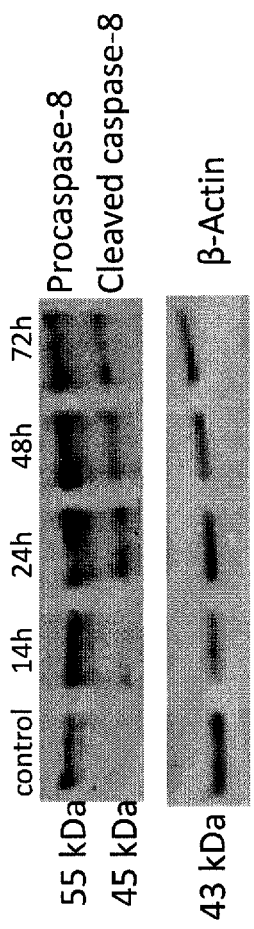
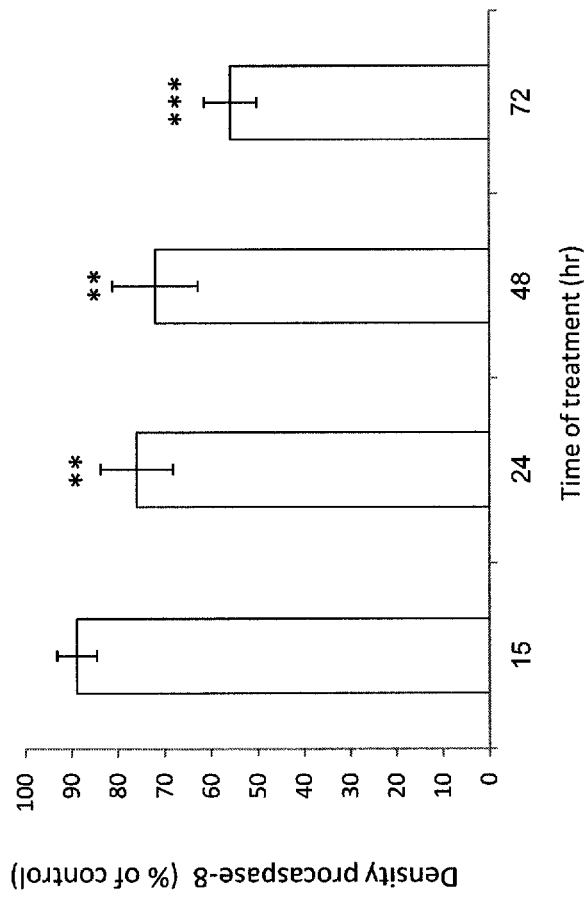
Figure 18A
Figure 18B

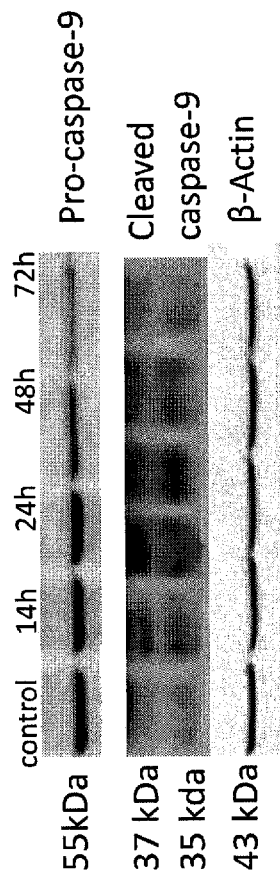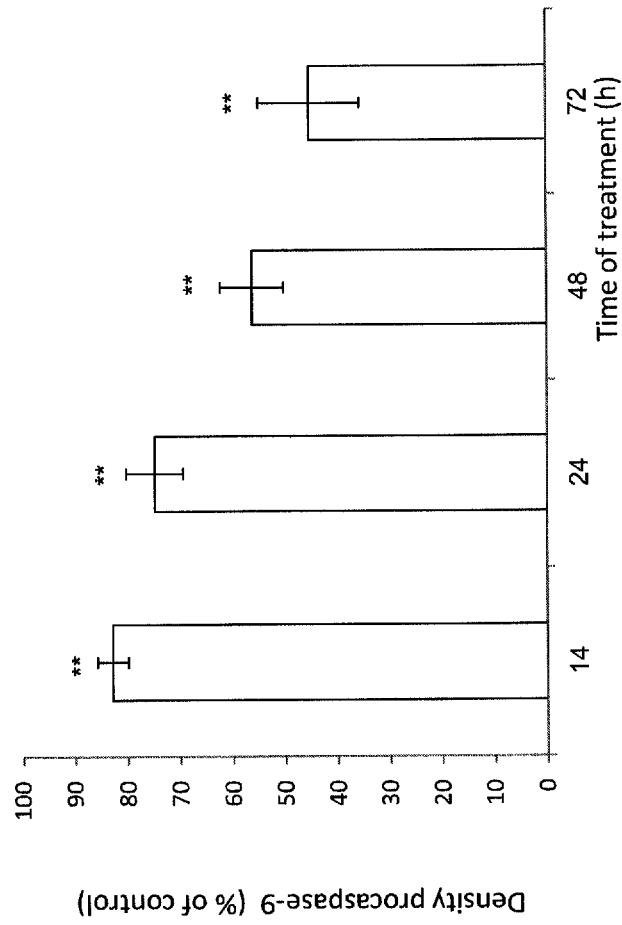
Figure 19A
Figure 19B

TREATMENT OF CANCER

CROSS REFERENCE TO RELATED APPLICATIONS

This patent application is a U.S. National Phase filing of commonly owned PCT Application No. PCT/IL2014/050525, filed Jun. 10, 2014, which is based on and claims the benefit of the filing date of U.S. Provisional Patent Application Ser. No. 61/833,463, filed Jun. 11, 2013, both of which are incorporated herein by reference in their entirety.

FIELD OF INVENTION

Embodiments of the invention relate to treatment of cancer.

BACKGROUND OF THE INVENTION

*Dittrichia viscosa*, formerly known as *Inula Viscosa* (IV) belongs to the Compositae family (common name "sticky fleabane") and is a perennial weed with sticky leaves, native to the Mediterranean Basin. It grows on hillslopes, damp habitats and roadsides. In folklore medicine, this plant is used for therapeutic purposes, such as a topical anti-inflammatic, diuretic, haemostatic, antiseptic, antipyretic, antiphlogistic and in the treatment of diabetes. Aqueous extracts of IV were shown to exhibit antifungal activity in vitro and antibacterial activity. Plants of the Composite family produce a wide array of sesquiterpenoid compounds, especially sesquiterpene lactones (SLs), as their main secondary metabolites. SLs have been identified as the active constituents of several medical plants used in traditional medicine, with a wide spectrum of biological activities including, anti-inflammatory and fungicidal properties.

Cancer is a disease characterized primarily by an increase in the number of abnormal cells derived from a given normal tissue, invasion of adjacent tissues by these abnormal cells, or spread of malignant cells to distant sites (metastasis).

Colorectal cancer is a relatively common form of cancer stemming from uncontrolled cell growth in the colon or rectum. Colorectal cancer is the second leading cause of cancer related death in the western world. Although colorectal cancer may be easily screened for using techniques such as colonoscopy, if not detected at an early stage, colorectal cancer may spread to other bodily organs, and may even be deadly. Age, diet, polyps, personal and familial medical history and chronic inflammation of the colon (e.g. ulcerative colitis) are known risk factors for this disease. The disease is equally prevalent in men and woman and the incidence of colon cancer is increasing. Although the mortality rate is decreasing due to screening tests, 5-year survival rates are still around 60%. First line treatment is surgery, however the majority of colorectal cancer patients are not candidates for curative local surgery, thus requiring chemotherapy. The effectiveness of chemotherapy treatment has been limited by the side effects and by development of resistance. In order to combat the problem of side effects and chemo-resistance, alternative therapies are required for the treatment of colorectal cancer.

SUMMARY OF THE INVENTION

The present invention relates, in some embodiments, to compositions and methods for treating colorectal cancer by administering to a subject an effective amount of a *dittrichia viscosa* (DV) extract.

According to one aspect, the present invention provides a method for treating colorectal cancer in a subject in need thereof, the method comprising administering to the subject a pharmaceutical composition comprising a therapeutically effective amount of a water extract derived from *dittrichia viscosa* leaves, thereby treating colorectal cancer in a subject.

In some embodiments, said *dittrichia viscosa* leaves are harvested prior to the blooming phase. In another embodiment, said *dittrichia viscosa* are cultivated *dittrichia viscosa* plants.

In another embodiment, the extract is administered in a dose of 8-80 mg/kg. In another embodiment, the extract is administered in a dose of 10-60 mg/kg. In another embodiment, the extract is administered in a dose of 12-24 mg/kg.

In some embodiments, said extract is in liquid form. In another embodiment, the amount of the extract is from about 0.01% to about 99.9% (w/w) compared to the total weight of the composition. In another embodiment, the amount of the extract is from about 0.01% to about 30% (w/w). In additional embodiments, said extract is in dried powder form.

In another embodiment, the composition is administered at least twice weekly. In another embodiment, the composition is administered at least three times weekly. In another embodiment, the composition is administered over at least 3 weeks.

In another embodiment, said administering is selected from intravenously, intratumorally, intraperitoneally or intramuscularly administration. In another embodiment, said administering is intraperitoneally administration. In another embodiment, said administering is systemic administration.

In another embodiment, the pharmaceutical composition further comprises a pharmaceutically effective excipients, diluent and/or carrier. In another embodiment, the composition comprises at least one additional active agent.

According to another aspect, the present invention provides a pharmaceutical composition comprising a water extract derived from *dittrichia viscosa* leaves for use in treating colorectal cancer in a subject.

According to another aspect, the present invention provides use of a water extract derived from *dittrichia viscosa* leaves for the preparation of a medicament for treating colorectal cancer in a subject in need thereof.

In some embodiments, the pharmaceutical composition is formulated for an administration regimen selected from intravenously, intratumorally, intraperitoneally or intramuscularly administration. In another embodiment, the pharmaceutical composition is formulated for intraperitoneally administration. In another embodiment, the pharmaceutical composition is formulated for systemically administration.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE FIGURES

Non-limiting examples of embodiments of the invention are described below with reference to figures attached hereto that are listed following this paragraph.

FIG. 5. Effect of *Inula viscosa* extract on cell cycle distribution of HCT116 cells.

FIG. 7. Effect of *Inula viscosa* extract on cell cycle distribution of Colo320 cells.

FIGS. 18A-C. Western blot analysis on the expression levels of procaspas-8 and cleaved caspsae 8 following treatment of Colo320 cells with *Inula viscosa* extract. 18A: Western blotting results; upper bands, uncleaved caspase-8, middle bands, cleaved caspase-8 and lower bands are -actin. 18B and C: Average expression levels of procaspase-8 (18B) and cleaved caspase-8 (18C); density values were calculated as a control from the proper -actin and as a percent of control.

FIGS. 19A-C. Western blot analysis on the expression levels of procaspas-9 and caspase 9 following treatment of HCT116 cells with *Inula viscosa* extract. 19A: Western blotting results; upper bands, uncleaved caspase-9, middle bands, cleaved caspase-9 and lower bands are -actin. 19B and C: Average expression levels of procaspase-8 (19B) and cleaved caspase 9 (19C); density values were calculated as a control from the proper -actin and as a percent of control.

DETAILED DESCRIPTION OF THE INVENTION

The present invention provides, in some embodiments, compositions and methods for treating colorectal cancer by administration to a subject an effective amount of a *dittrichia viscosa* (DV) extract.

In the detailed description below, results of experiments in animals that were carried out to determine effects of administration of *dittrichia viscosa* leaves aqueous extract in animals are provided and described. Implications of the experimental results for the use and administration of DV extract in humans in accordance with embodiments of the invention are discussed. Protocols for administration of DV to treat colon and/or rectal cancer in humans are provided. The experimental results indicate that DV treatment protocols in accordance with embodiments of the invention may be advantageous in treating colon cancer.

Figure 2A:
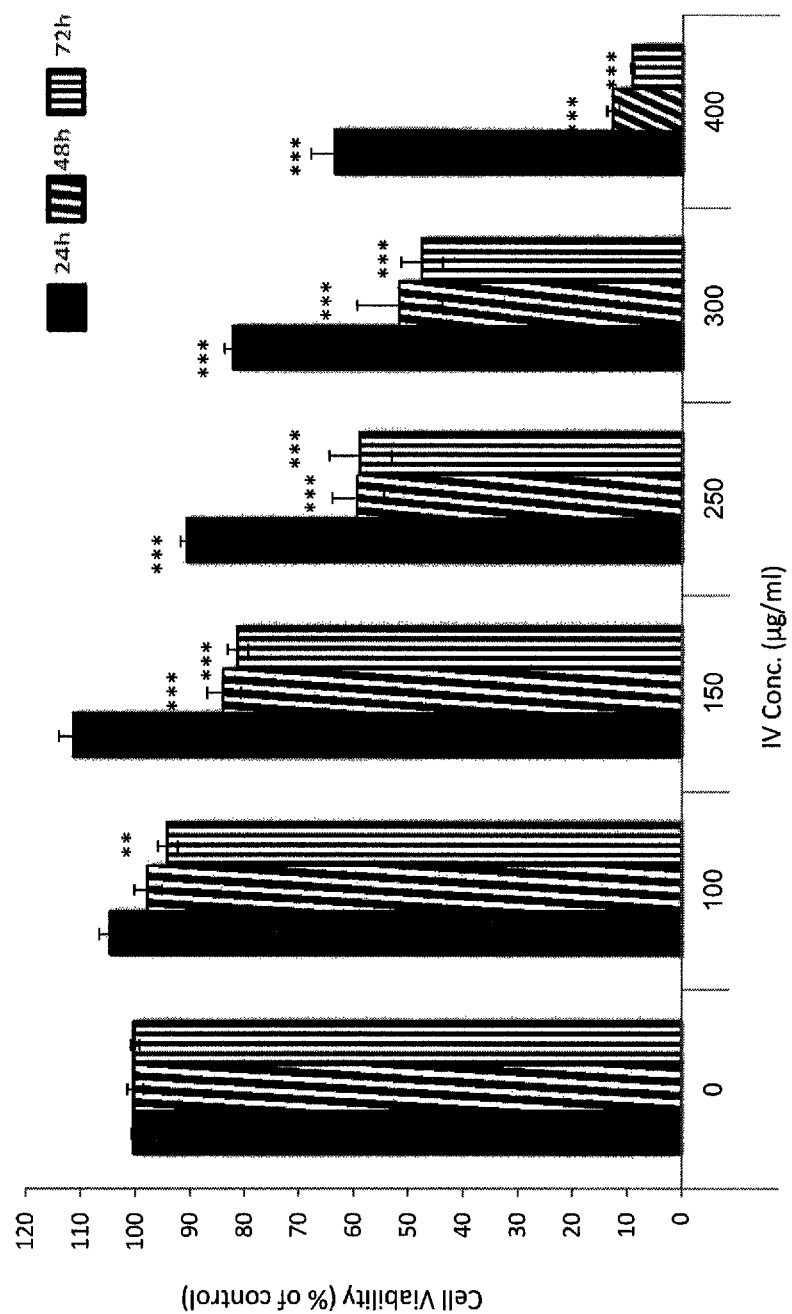
FIGS. 2A-B. Effect of *Inula viscosa* (IV) extract on the viability of HCT116 (2A) and Colo320 (2B) cells.
Figure 25:
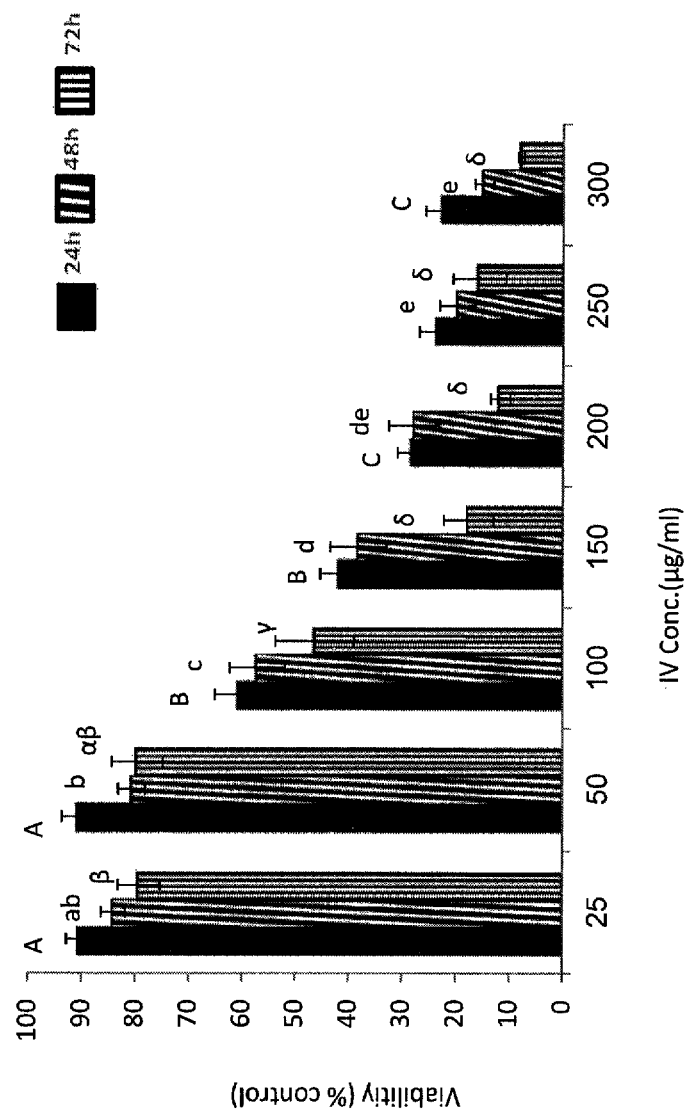
FIG. 25. Effect of *Inula viscosa* (IV) extract on the viability of MC38 cells.

As exemplifies herein below, water extract of DV leaves is effective against human colorectal cancer cell lines in inhibiting cell proliferation (FIGS. 2A-B and 25), inhibiting DNA synthesis (FIGS. 3A-B and 26), and inducing apoptosis. Moreover, the present invention shows, for the first time, colorectal cancer treatment in vivo, using water extract of DV leaves (e.g., FIGS. 32 and 33).

Figure 1A:
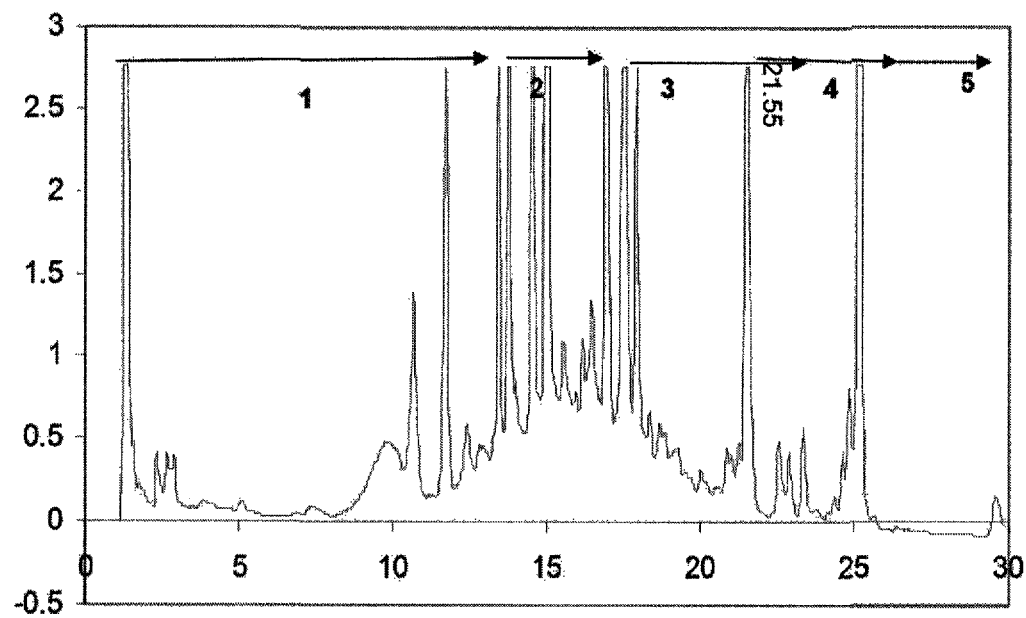
FIGS. 1A-B. Reversed phase HPLC profile of (1A) water extract from *Inula viscosa* (IV) and (1B) ethanol extract from IV, detected at 220 nm.
Figure 1B:
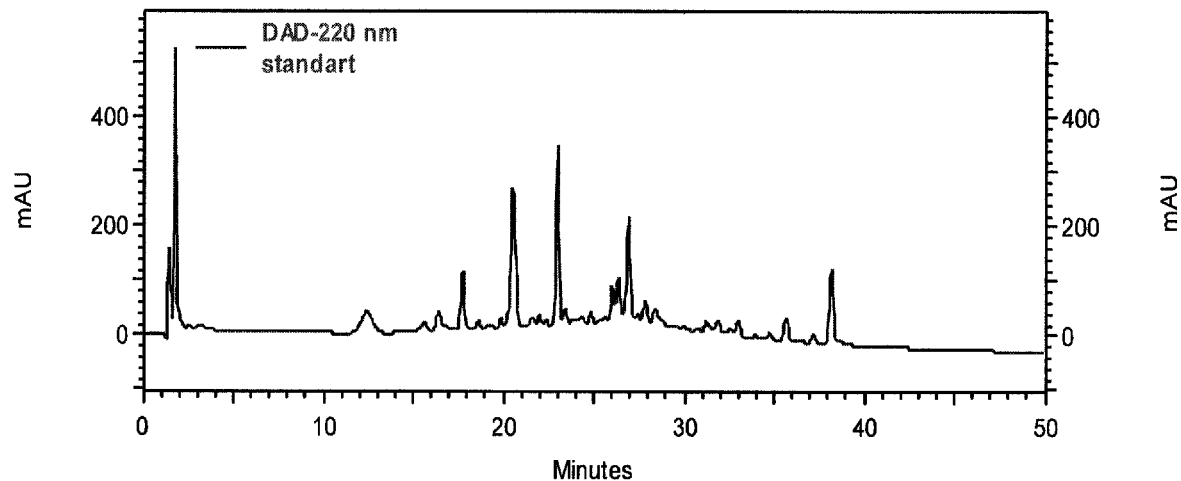

Without being bound by theory, it is suggested that water extract of *dittrichia viscosa* leaves impacts growth and development of cancer cells by preventing cell proliferation, inhibiting DNA synthesis and by inducing programmed cell death. As demonstrated herein below, DV leaves water extracts contain significantly more secondary metabolites (including antioxidants and/or proliferation inhibitors) as opposed to ethanol extract (FIG. 1, shown as peaks within 12-15 minutes).

*Dittrichia viscosa* (DV) or interchangeably *Inula viscose* (IV), which is a member of the Compositae family, is a plant that grows to about 1 to 1.5 meter in height. The leaves and stems of the plant are coated with a sticky resin. Its flowers which blossom mainly during August to November are widely rounded and are yellowish in color. Roots are deep brown in color, whitish on the inside and have a characteristic smell. The plant is also known in Arabic as Rasen and typically grows in the Mediterranean basin.

Figure 39:
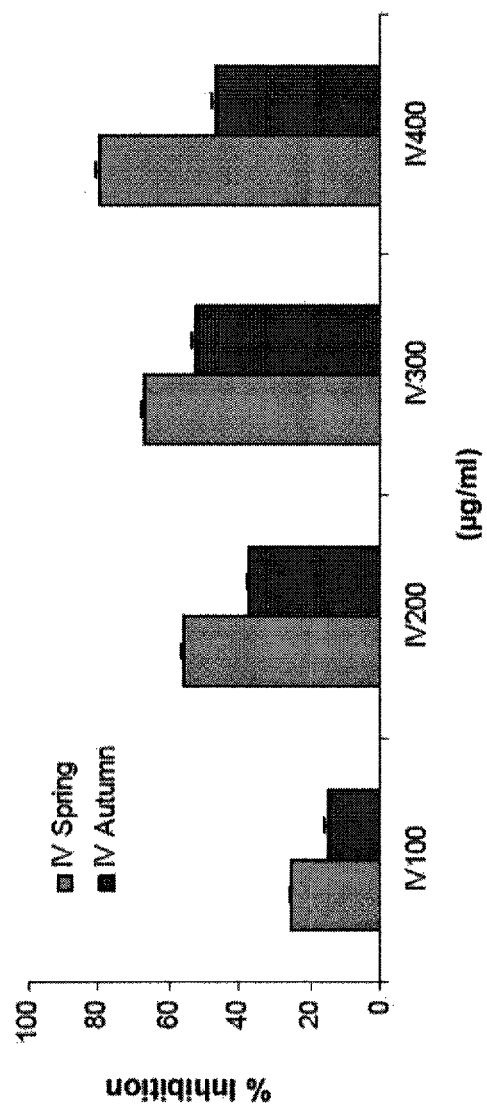
FIG. 39. The effect of aqueous extract from *Inula viscosa* leaves picked in fall or spring on cell proliferation (XTT) in cancerous cells.

The present invention is also based, in part, on the finding that the anti-proliferative effect of water extract derived from DV leaves is significantly higher when the leaves are harvested prior to the plant blooming phase, e.g., in the spring, rather than in the autumn (FIG. 39). In some embodiments of the invention, leaves of DV are harvested (i.e., collected) prior to the plant's blooming phase, or at a phase other than the plant's blooming phase. A skilled artisan is well capable of determining the blooming phase of DV, which is typically during autumn (e.g., from September to November in the northern hemisphere and from March to May in the southern hemisphere). Thus, according to some embodiment, the *Inula viscosa* leaves are harvested prior to autumn. In another embodiment, the DV leaves are harvested during spring (e.g., such as from March to May in the northern hemisphere and from September to November in the southern hemisphere).

As used herein, the term "harvested prior to the blooming phase" or "harvested prior to autumn" refers to a period of time wherein the amount of particles within DV leaves extract is higher compared to the blooming phase of DV, thereby forming extract comprising significantly more secondary metabolites (e.g., antioxidants). In some embodiments, said prior to is at least 1 day, at least 2 days, at least 3 days, at least 4 days, at least 5 days, at least 6 days, at least 1 week, at least 2 weeks, at least 3 weeks or at least 4 weeks prior to the blooming phase of the plant or correspondingly prior to autumn.

In some embodiments, an aqueous extract of DV is prepared according to the method described in Rozenblat et al. biochemical pharmacology 75 (2008) 369-382, which is incorporated here by reference for all purposes as if fully set forth herein. In another embodiment, fresh leaves of DV are collected and dried for at least 5, at least 10, at least 15, at least 20 or at least 24 hours. Drying the leaves may be in the sun, or alternatively in an oven or the like. In another embodiment, said leaves are left for further drying in room temperature for about 1-7 days, about 2-6 days, about 3-5, or about 4 days. In another embodiment, said leaves are then homogenized in distilled water 1:2-1:12 (w/v). In another embodiment, the homogenate is then filtered (such as through Whatman No. 1 filter paper) and centrifuged (such as at 20,000 g for 10 min). The supernatant may then be frozen such as in liquid nitrogen and dried such as in a lyophilizer (0.07 mbar, 48° C.), freeze drying or spray drying or the like to produce powdered watery DV extract. According to embodiments of the invention, DV extract may be used using infusion, maceration, decoction or distillation. Additionally, processes such as spray drying or evaporation may be used in place of lyophilization (freeze drying).

In some embodiment, aqueous extract of DV is prepared by methods which do not include an initial drying step. In such embodiments, aqueous extract of DV is prepared by collecting fresh DV leaves and homogenizing said leaves in distilled water 1:2-1:12 (w/v). In additional embodiments, the homogenate is then filtered, centrifuged, frozen and dried in a lyophilizer to produce powdered watery DV extract.

In some embodiments, an aqueous extract of DV is prepared using a water to leave ratio of 1:2-1:10. In some embodiments, an aqueous extract of DV is prepared using a water to leave ratio of 1:2-1:8. In some embodiments, an aqueous extract of DV is prepared using a water to leave ratio of 1:3-1:6. In some embodiments, an aqueous extract of DV is prepared using a water to leave ratio of 1:3-1:5. In some embodiments, an aqueous extract of DV is prepared using a water to leave ratio of 1:4. A water to leave ratio, as used herein, refers to a weight ratio.

Pharmaceutical Compositions

In an embodiment of the invention, DV extract is combined with at least one pharmaceutically acceptable excipient to form a pharmaceutical composition. In an embodiment of the invention, the pharmaceutical composition is adapted for human or animal use via oral, rectal, vaginal, topical, nasal, ophthalmic, transdermal, subcutaneous, intramuscular, intraperitoneal or intravenous administration.

In one embodiment, the composition is administered in a local rather than systemic manner, for example, via injection of the composition directly into a specific region of a patient's body.

The pharmaceutical compositions according to an embodiment of the invention may be conveniently presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe.

The pharmaceutical compositions according to embodiments of the invention are generally administered in the form of a pharmaceutical composition comprising at least one active component together with a pharmaceutically acceptable carrier or diluent.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the components of this invention can be combined with various sweetening agents, flavoring agents, coloring agents, emulsifying agents and/or suspending agents, as well as such diluents as water, ethanol, propylene glycol, glycerin and various like combinations thereof.

The compositions according to embodiments of this invention may also be administered in a controlled release formulation such as a slow release or a fast release formulation. Such controlled release dosage composition may be prepared using methods well known to those skilled in the art.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

Pharmaceutical compositions according to embodiments of the invention may contain an active amount of 0.01%-99.9%, 0.1%-95%, 0.1%-70%, preferably 1%-30% of DV extract.

In an embodiment of the invention, the dosage of DV extract is between 5 mg/kg and 20 mg/kg. In an embodiment of the invention, the daily dosage of DV extract is between 10 and 15 mg/kg. The dosage may be administered daily, three times a week, or once a week. In another embodiment, the extract is administered in a dose of at least 5 mg/kg, at least 6 mg/kg, at least 7 mg/kg, at least 8 mg/kg, at least 9 mg/kg, at least 10 mg/kg, at least 11 mg/kg or at least 12 mg/kg. In another embodiment, the extract is administered in a dose of at most 100 mg/kg, at least 90 mg/kg, at least 80 mg/kg, at least 70 mg/kg, at least 60 mg/kg, at least 50 mg/kg, at least 40 mg/kg, at least 30 mg/kg, at least 29 mg/kg, at least 28 mg/kg, at least 27 mg/kg, at least 26 mg/kg, at least 25 mg/kg or at least 24 mg/kg.

In an embodiment of the invention, the dosage administered to humans is between 300 and 1200 mg. In an embodiment of the invention, the dosage administered to humans is between 600 and 1000 mg. The dosage may be administered daily, three times a week, or once a week.

According to an embodiment of the invention, DV is administered to a patient in need thereof in combination with an additional anti-cancer agent. In an embodiment of the invention, the anti-cancer agent is selected from the group consisting of bevacizumab, cetuximab, panitumumab, fluorouracil, capecitabine, tegafur-uracil, leucovorin, irinotecan and oxaliplatin.

Pharmaceutical Use

According to an embodiment of the invention, DV is administered to a patient having a high risk of colorectal cancer. According to an embodiment of the invention, the patient having high risk is a patient with a high intake of fat, alcohol, or red meat; an obese patient; a diabetic patient; a patient who has smoked cigarettes; a sedentary patient; a patient suffering from inflammatory bowel disease; a first degree relative of a colorectal cancer patient; a patient suffering from Gardner syndrome; a patient suffering from familial adenomatous polyposis; Hereditary nonpolyposis colorectal cancer, (Lynch syndrome); a patient above 50 years of age; a patient having a history of colorectal cancer or polyps; a patient who had previously been subjected to radiation of the abdominal area; a patient in which benign polyps have been detected in the colorectal region; a patient having a history of ovarian, uterine or breast cancer, and a patient having a low-fiber diet.

According to an embodiment of the invention, DV is administered to a patient having chemotherapy resistant colorectal cancer. According to an embodiment of the invention, DV is administered to a patient having recurrent colorectal cancer.

According to an embodiment of the invention, DV is administered to a patient having colorectal cancer characterized as adenocarcinoma, lymphoma or squamous cell carcinoma.

In the description and claims of the present application, each of the verbs, "comprise" "include" and "have" and conjugates thereof, are used to indicate that the object or objects of the verb are not necessarily a complete listing of components, elements or parts of the subject or subjects of the verb.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

EXAMPLES

Example 1

Manufacture of Aqueous *Dittrichia Viscosa* (*Inula viscosa*) Extract

Fresh leaves of *dittrichia viscosa* were collected from a field near Ramat Gan, Israel. The leaves were dried for two days in the sun and for another four days at room temperature. The dried leaves were homogenized in distilled water at a ratio of 1:8 (weight/volume). The homogenate was collected, filtered through filter paper (Whatman No. 1) and centrifuged at 20,000×g for 10 minutes (min). The supernatant was then removed, boiled for 40 min, in order to reduce volume, filtered again and dried in a lyophilizer (0.07 millibar, −48° C.). The resulting lyophilized powder was dissolved in phosphate buffered saline (PBS) to obtain 2-4% stock solutions which were then diluted as necessary to achieve appropriate concentrations with PBS (for in vivo studies) or cell medium (for in vitro studies) to form DV extracts designated as IV extract.

Example 2

Effect of *Inula viscosa* Extract on Cell Proliferation in Colon Cancer Cell Lines A cell proliferation assay was performed in which various concentrations of IV extract were tested on inhibition of cell proliferation using two lines of cell culture, human colon adenocarcinoma cell lines HCT116 (a well differentiated cell line) and Colo320 (a poorly differentiated cell line), and murine adenocarcinoma cell line MC38. The assay was an "XTT" assay in which cell viability was tested by determining the ability of metabolically active cells to reduce a tetrazolium salt, XTT (sodium 3'-[1-(phenylaminocarbonyl)-3,4-tetrazolium]-bis(4-methoxy-6-nitro)benzene sulfonic acid hydrate) to orange colored compounds of formazan, a soluble dye, which was measured at a wavelength of 450 nanometers (nm).

HCT116, Colo320 and MC38 cells were seeded in 100 μl of medium, using 96-well plates at a cell density of $10^4$ cells per well. After 24 hours, IV extract was added in several concentrations: 100, 150, 250, 300 and 400 micrograms per milliliter (μg/ml) for HCT116 and Colo320 cells and in concentrations: 25, 50, 100, 150, 200, 250 and 300 μg/ml for MC38 cells. Cells were incubated for 24, 48 and 72 hours in $CO_2$ incubator at 37° C. Controls wells were medium-treated wells. On the day of the assay, viability levels were determined according to the manufacturer's instructions using an ELISA reader (Bio Tek) at 450 nm wave and subtracted from the reference absorbance at 620 nm. At least four independent experiments were performed each conducted in five replicates.

Figure 2B:
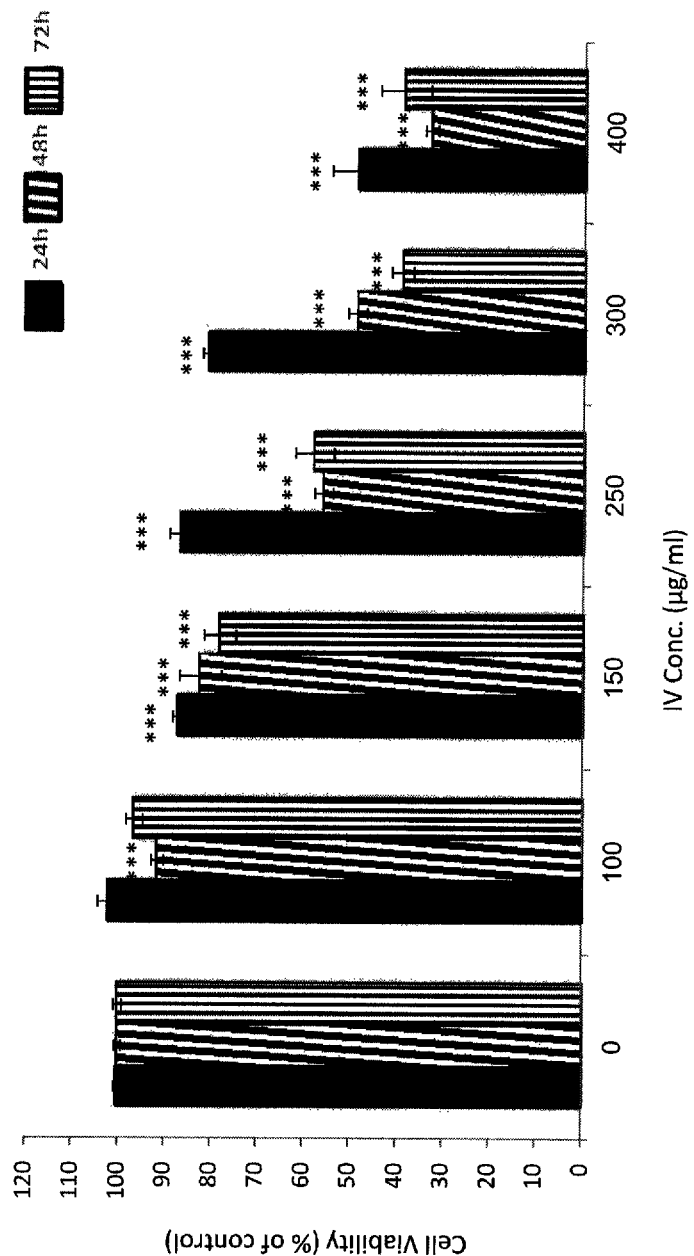

IV extract at concentrations of 100 μg/ml significantly decreased cell viability after 72 hours of incubation in HCT116 cells and after 48 hours of incubation for Colo320 cells. Significant reduction of cell viability after 24 hours of incubation was evident at a concentration of 250 μg/ml for HCT116 cells (FIG. 2A) and at 150 μg/ml for Colo320 cells (FIG. 2B).

IV extract at a concentration of 25 μg/ml significantly decreased cell viability after 72 hours of incubation in MC38 cells. IV extract at a concentration of 50 μg/ml significantly decreased cell viability after 48 hours of incubation in MC38 cells. IV extract at a concentration of 100 μg/ml significantly decreased cell viability after 24 hours of incubation in MC38 cells (FIG. 2S).

Based on the above experiment, $IC_{50}$ (half maximal inhibitor concentration) values for IV extract, in μg/ml, were determined for the two cell lines at the three treatment times, and are displayed in table 1 below.

TABLE 1

IC$_{50}$ values for IV extract (µg/ml)

| Cell line | Duration of Treatment | | |
|---|---|---|---|
| | 24 hours | 48 hours | 72 hours |
| HCT116 | 505.4 | 280.8 | 270.2 |
| Colo320 | 445.5 | 301.5 | 300 |

Cytotoxicitiy Determination (LDH Release) of IV Extract

In order to test the cytotoxicity levels of IV extract in the cells, LDH leakage assay was preformed. HCT116, Colo320 and MC38 cells were cultured in 96 well/plate following IV treatment (50, 100, 150, 200, 250, 300 and 350 µg/ml). 24 hours post treatment supernatant was removed to a new 96-well plate and reaction mixture (Diaphorase/NAD$^+$ and Iodotetrazolium chloride (INT) and sodium lactate) was added to each well. Plates were incubated for 30 minutes in room temperature in the dark. Cytotoxicity levels were measured in a 492 nm wavelength using ELISA reader. Three independent experiments each preformed in five replicates were preformed.

Figure 4A:
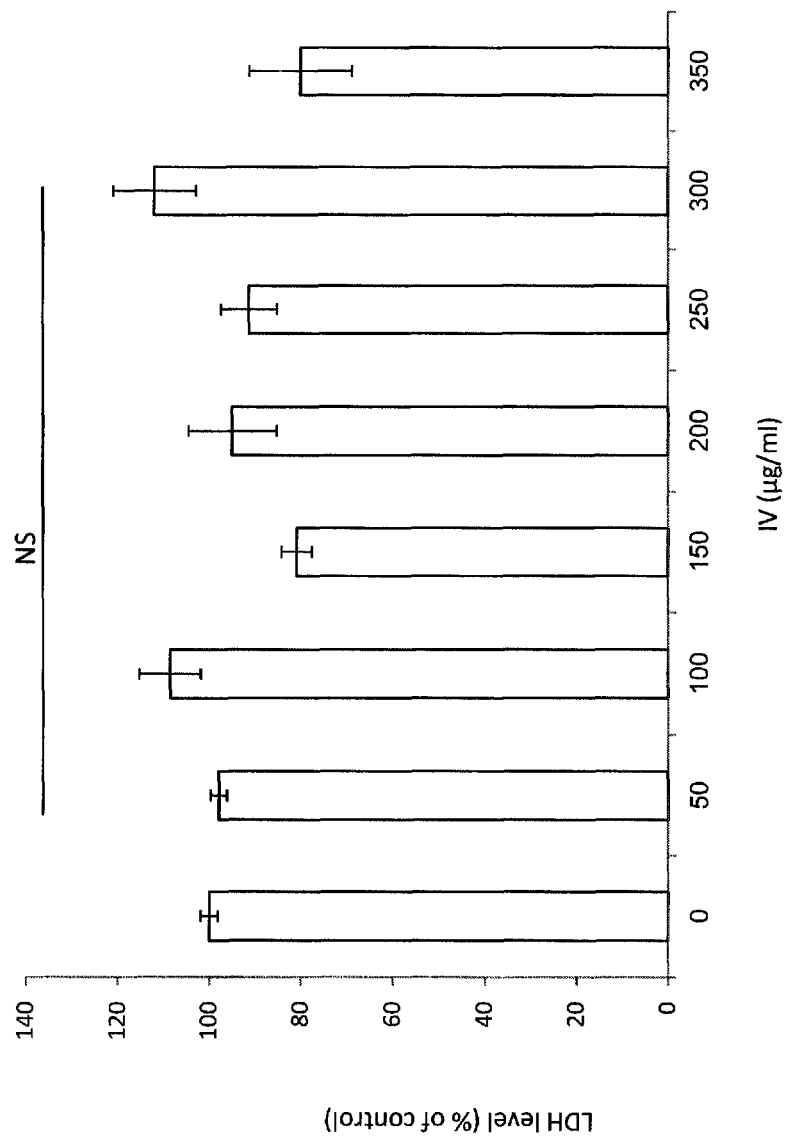
FIGS. 4A-B. Release of lactate dehydrogenase (LDH) into the culture medium of HCT116 (4A) and Colo320 (4B) cells.
Figure 4B:
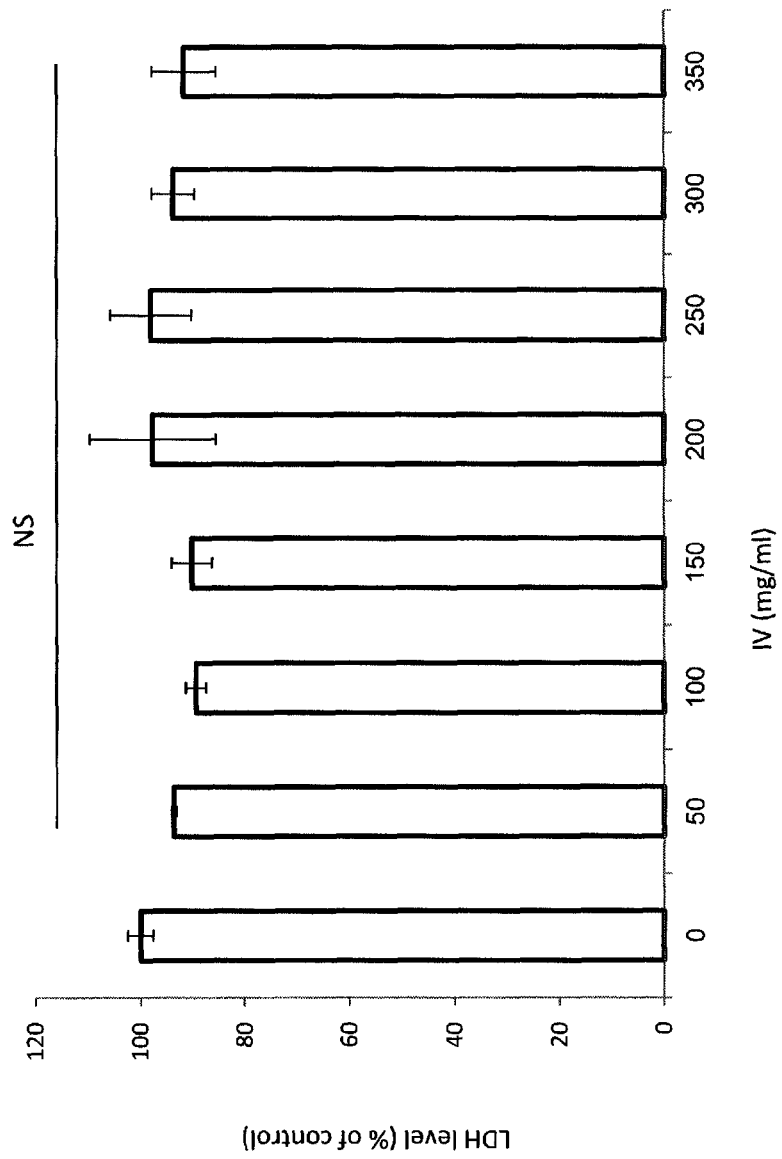
Figure 27:
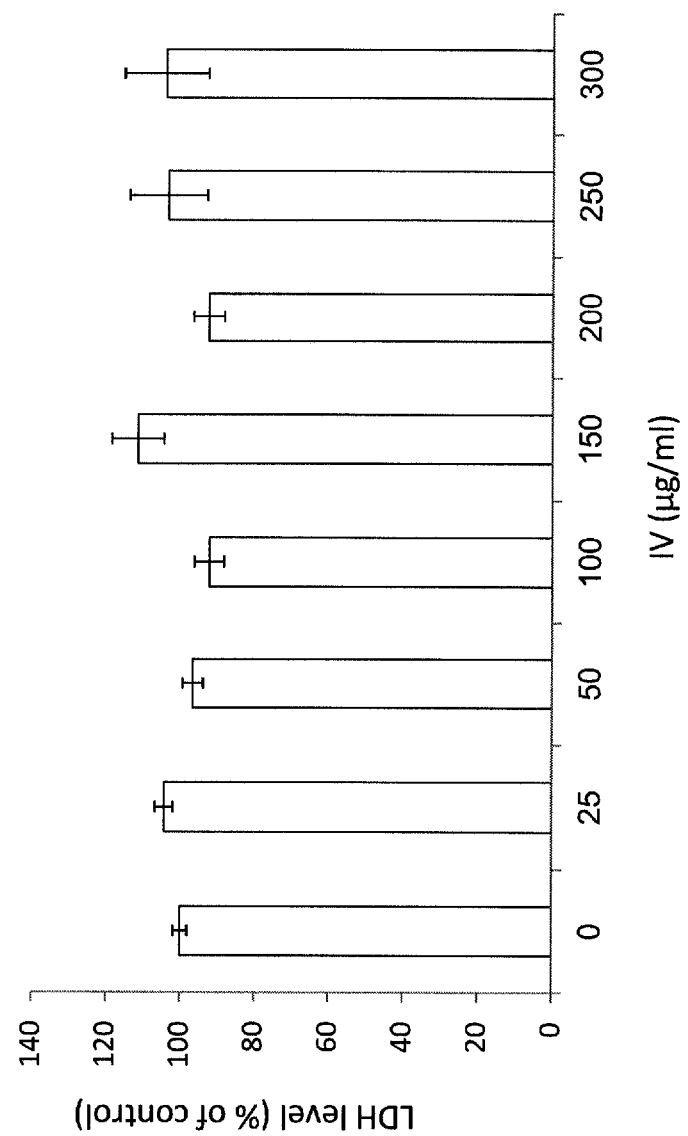
FIG. 27. Release of lactate dehydrogenase (LDH) into the culture medium of MC38 cells.
Figure 28A:
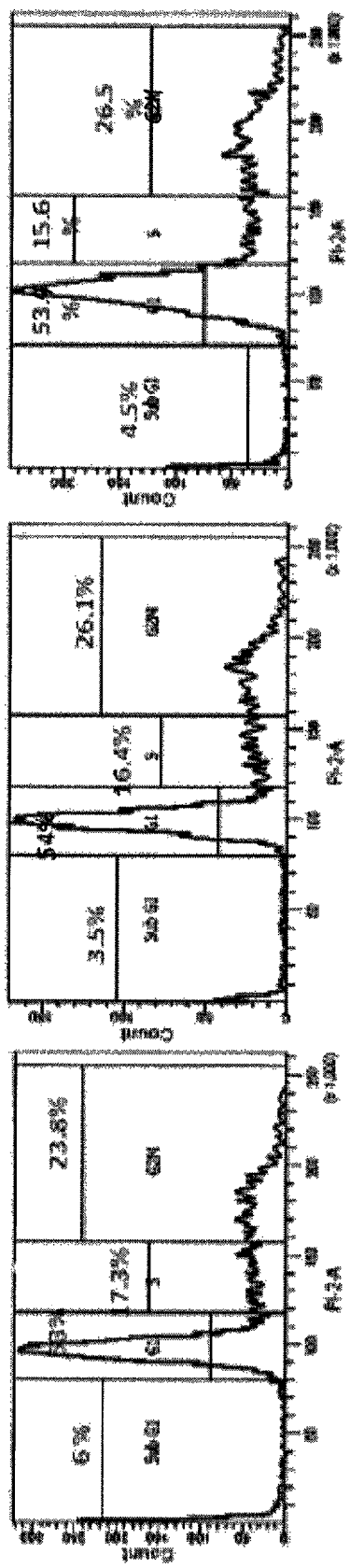
FIG. 28. Effect of *Inula viscosa* extract on cell cycle distribution of MC38 cells. Representative flow cytometric histograms for controls (28A) and treatments (28B) in each time of treatments are shown. Numbers in histograms show percentage of cells in each phase of the cell cycle.
Figure 28B:
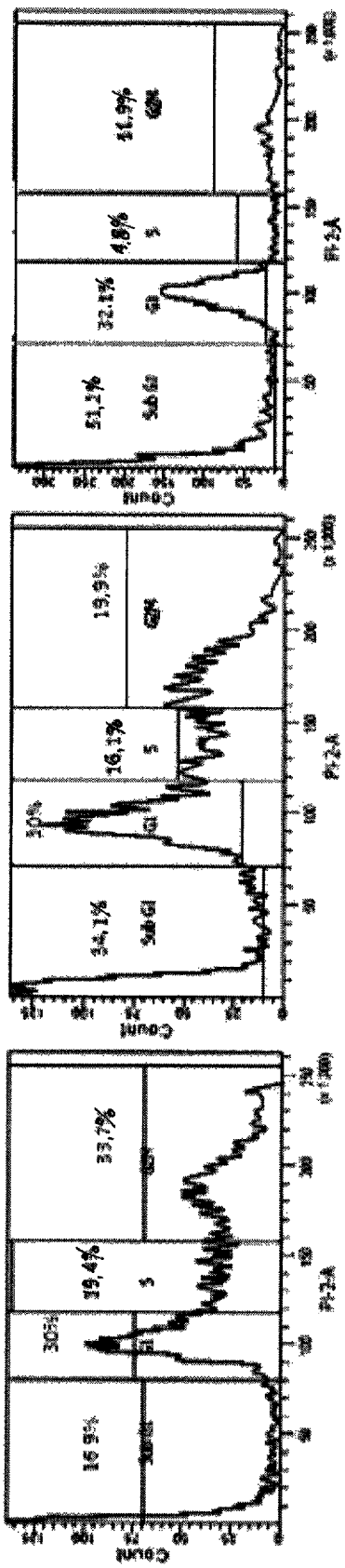
Figure 29:
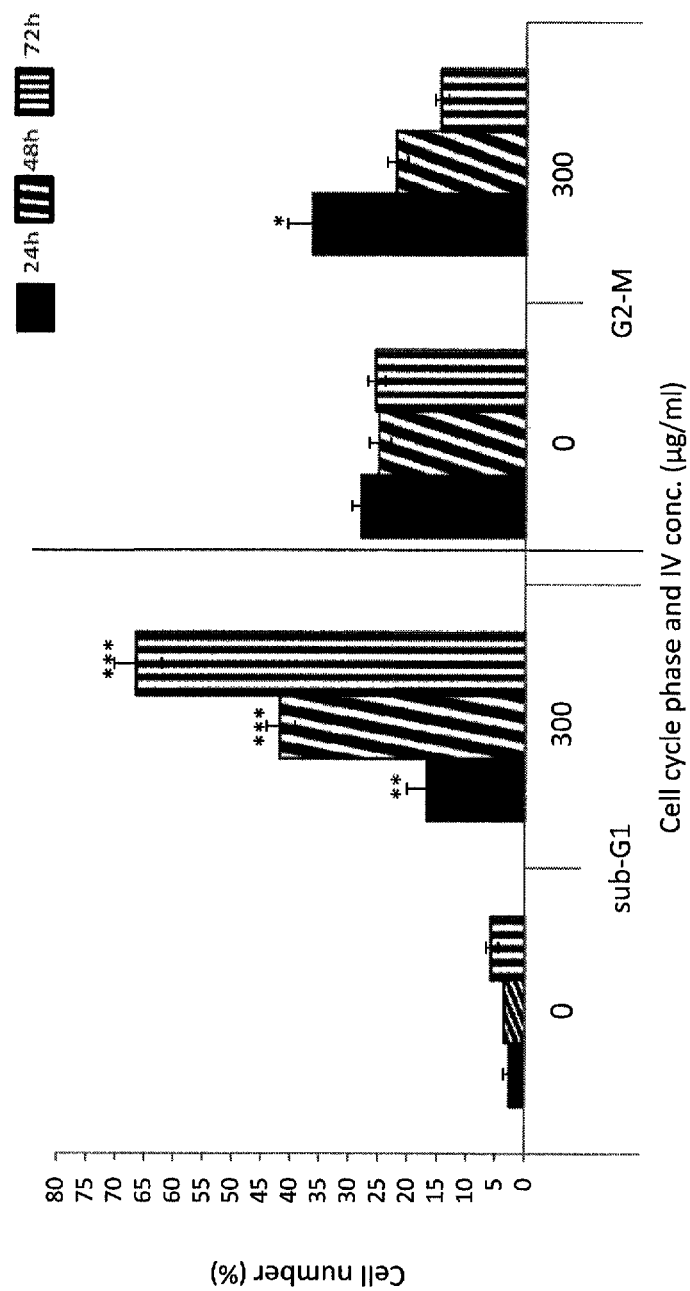
FIG. 29. Summary of percentage of cells in sub-G1 and G2/M phase following treatment of MC38 with *Inula viscosa* extract using FACS analysis.

According to FIGS. 4 and 27, no significant differences were observed in LDH levels, compared to control, in all concentrations tested in both cell lines. These results indicated that all the examined concentrations were not toxic to HCT116, Colo320 and MC38 cell lines.

The above experiment shows that IV extract is effective in inhibiting cell proliferation in colon cancer cell lines, and is not toxic to the cells at relatively low concentrations.

Example 3

Effect of *Inula viscosa* Extract on DNA Synthesis in Colon Cancer Cell Lines

As cancer cells divide, DNA replication occurs, in which the cell copies its own DNA. Inhibiting DNA synthesis in cancer cells may prevent cancer cells from dividing, thereby slowing the growth of cancer. DNA synthesis was examined in two human colon cancer cell lines using a 5-Bromo-2-uridine (BrdU) Labeling and Detection Kit III (Roche) which is based on the incorporation of BrdU to proliferating cells. BrdU is an analog of thymidine, therefore it can incorporate into newly synthesized DNA of proliferating cells. Levels of BrdU can be correlated to DNA synthesis in a cell using this method, in which monoclonal antibodies labeled with peroxidase specific for BrdU are used to detect the incorporated BrdU. The enzyme peroxidase catalyzes the cleavage of the peroxidase substrate that is added to the cell culture and produces a color reaction, thus indicating cells that were actively replicating their DNA. The color reaction may be measured by ELISA reader, at 492 nm and background absorption of 690 nm.

HCT116, Colo320 and MC38 cells were tripsinized and counted using hemocytometer. Cells were seeded in 96-well plates at a concentration of $10^4$ cell per well in 100 µl of medium. After 24 hours, IV extract was added in several concentrations: 50, 100, 150, 200, 250 and 300 µg/ml for 24, 48 and 72 hours in the presence of $CO_2$ in an incubator at 37° C. On the day of examination, 10 µM of BrdU reagent was added to each well, and the plates were incubated in the presence of $CO_2$ in an incubator for 4 hours. Next, cells were fixed with 0.5 molar (M) ethanol/HCl for 30 minutes in −20° C. Following fixation, cellular DNA was partially digested by nuclease treatment for 30 minutes in 37° C. wrapped with parafilm to avoid $CO_2$ leakage from the incubator. DNA synthesis was determined using an ELISA reader (BioTek). Experiments were repeated, at least, 3 times independently and conducted in 5 replicates. Data were presented as average of DNA synthesis percentage of the respective control.

At concentrations as low as 50 µg/ml, IV extract was effective in significantly lowering DNA synthesis in HCT116 (FIG. 3A), Colo320 (FIG. 3B) and MC38 cells (FIG. 26) relative to control cells to which no IV extract was administered. Upon increase in concentration of IV extract, DNA synthesis was further decreased in a dose dependent manner.

Figure 3A:
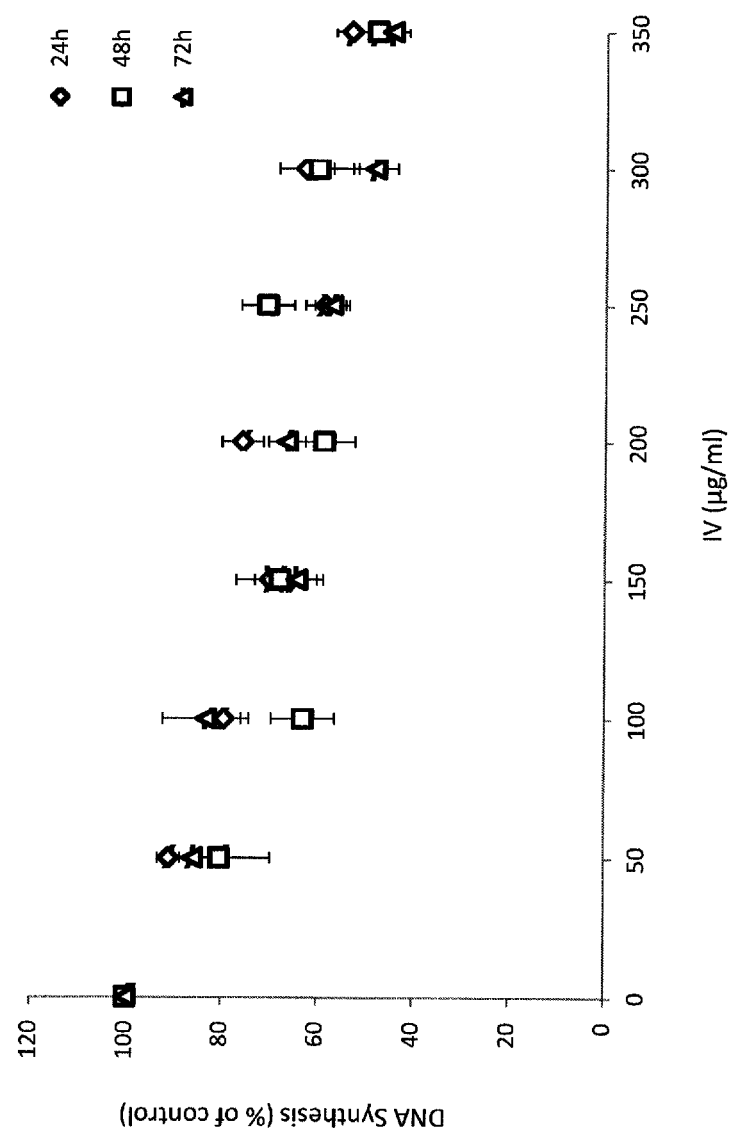
FIGS. 3A-B. Effect of *Inula viscosa* extract on DNA synthesis of HCT116 (3A) and Colo320 (3B).
Figure 3B:
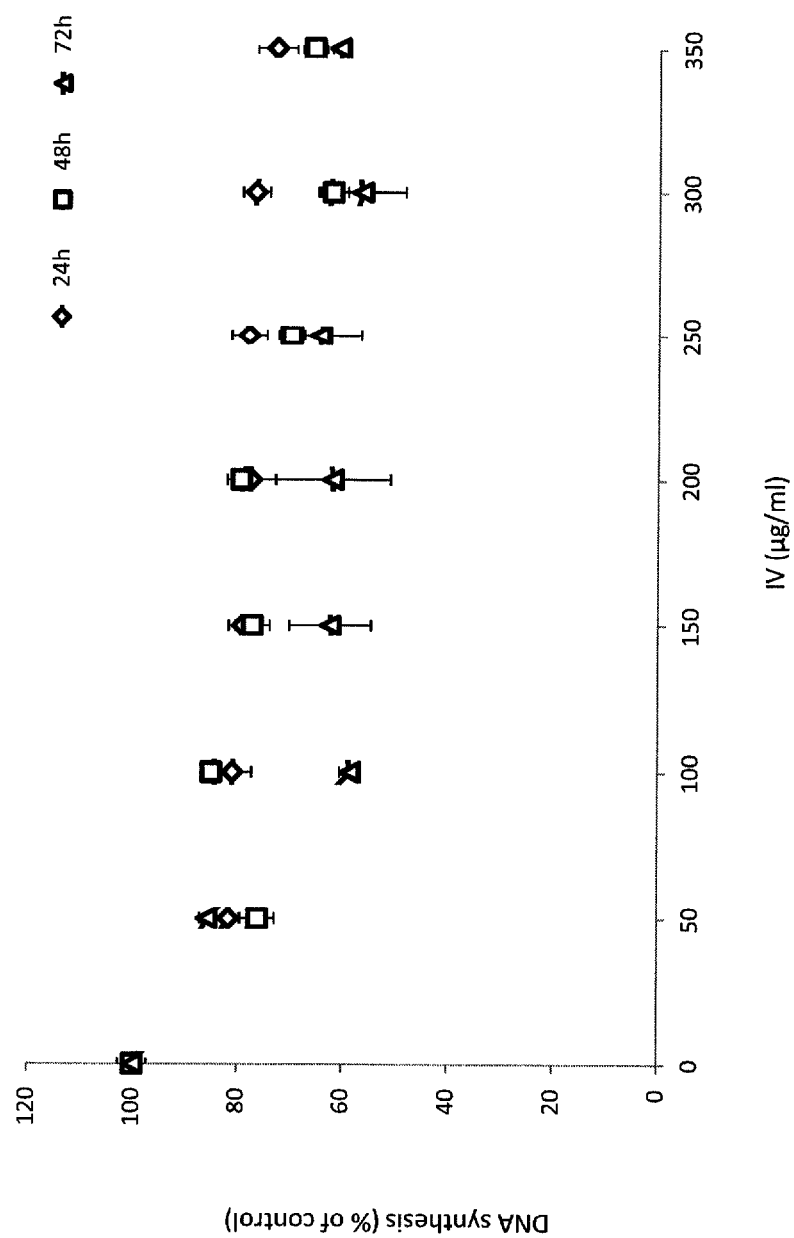
Figure 26:
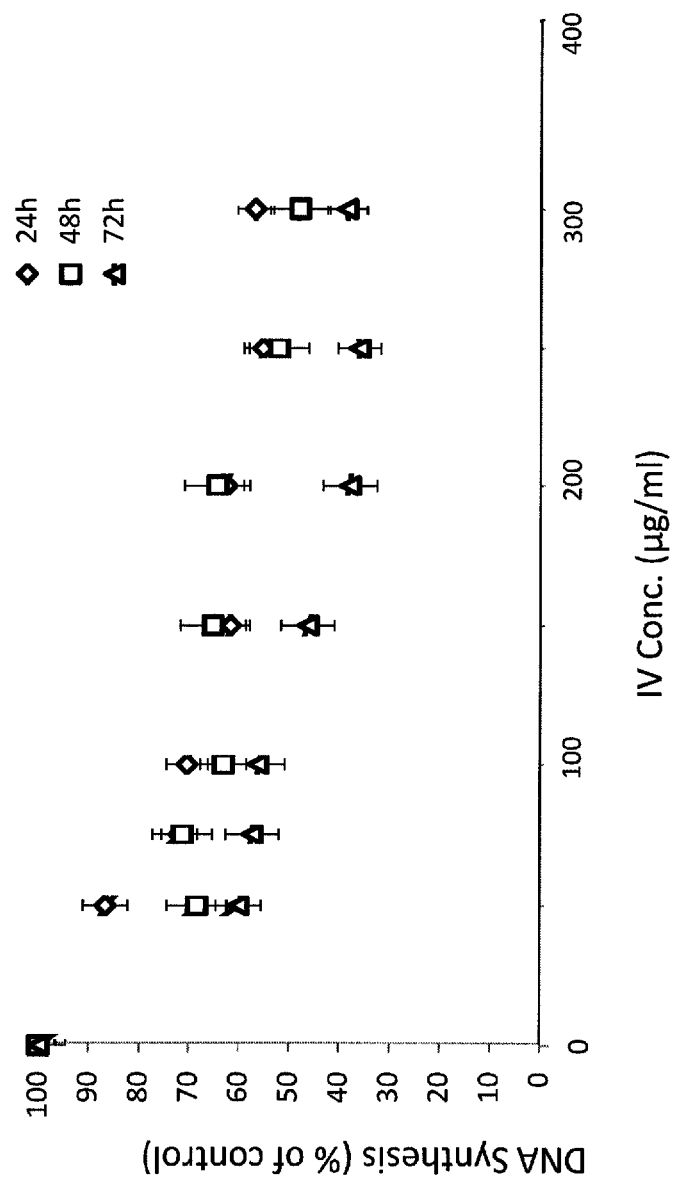
FIG. 26. Effect of *Inula viscosa* extract on DNA synthesis of MC38.

Example 3 shows that IV extract is effective against human colorectal cancer cell lines in inhibiting DNA synthesis (FIGS. 3A-B and 26).

Example 4

Effect of *Inula viscosa* Extract on Apoptosis (Controlled Cell Death) in Colon Cancer Cell Lines Quantization of apoptosis was performed by flow cytometry based on Annexin-V Fluorescein isothiocyanate (FITC) and propidium iodide (PI) double staining kit (MBL, USA). The apoptotic program is characterized by certain morphologic features. One of the earliest stages of apoptosis is loss of plasma membrane. In apoptotic cells, the membrane phospholipid phosphatidylserine (PS) is translocated from the inner (cytoplasmatic) to the outer face of the plasma membrane, thereby exposing PS to the external cellular environment. This process can be monitored by using Annexin V which is a calcium-dependent reagent that has high affinity for PS. In order to be able to distinguish between apoptosis and necrosis, cells were stained with FITC-labeled annexin V and PI. Annexin V binds to the externalized PS, whereas PI is able to penetrate the increasingly permeable plasma membrane during necrosis or later stages of apoptosis and binds to cellular DNA. Live cells are not stained.

Effect of IV Extract on Cell Cycle Distribution of HCT116, Colo320 and MC38 Cells Cells ($10^6$) were treated with 300 µg/ml of IV extract for 14-72 hours. At the end of treatments, cells were harvested, fixed and their DNA stained with PI. Quantitative analysis of DNA content in each phase was conducted by FACS as described above. Representative flow cytometric histograms for controls (A1-D1) and treatments (A2-D2) in each time of treatments are shown. Numbers in histograms show percentage of cells in each phase of the cell cycle. The histograms demonstrated are representative figures of five experiments each conducted in duplicates.

Figure 6:
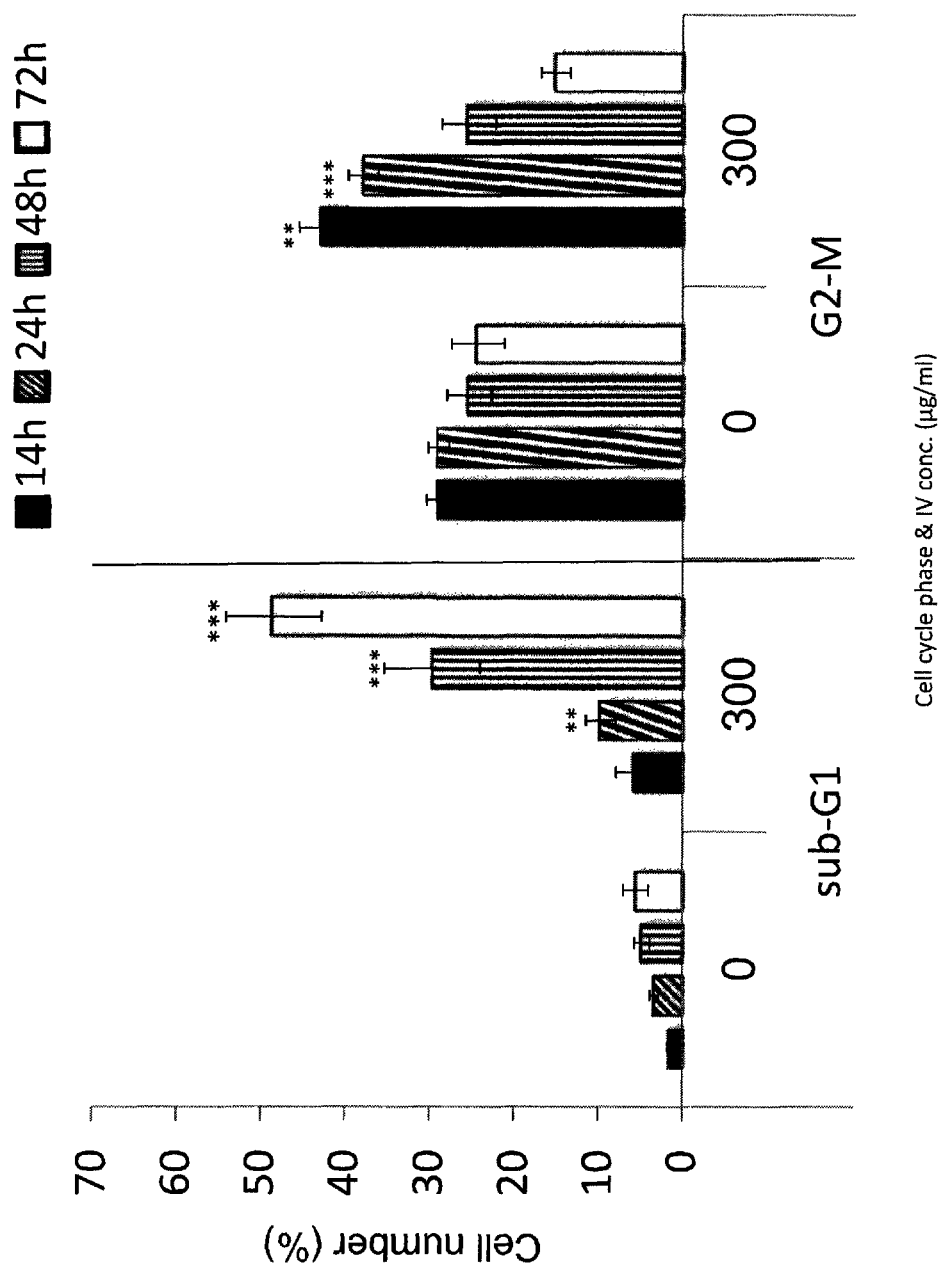
FIG. 6. Summary of percentage of cells in sub-G1 and G2/M phase following treatment of HCT116 with *Inula viscosa* extract using FACS analysis.
Figure 8:
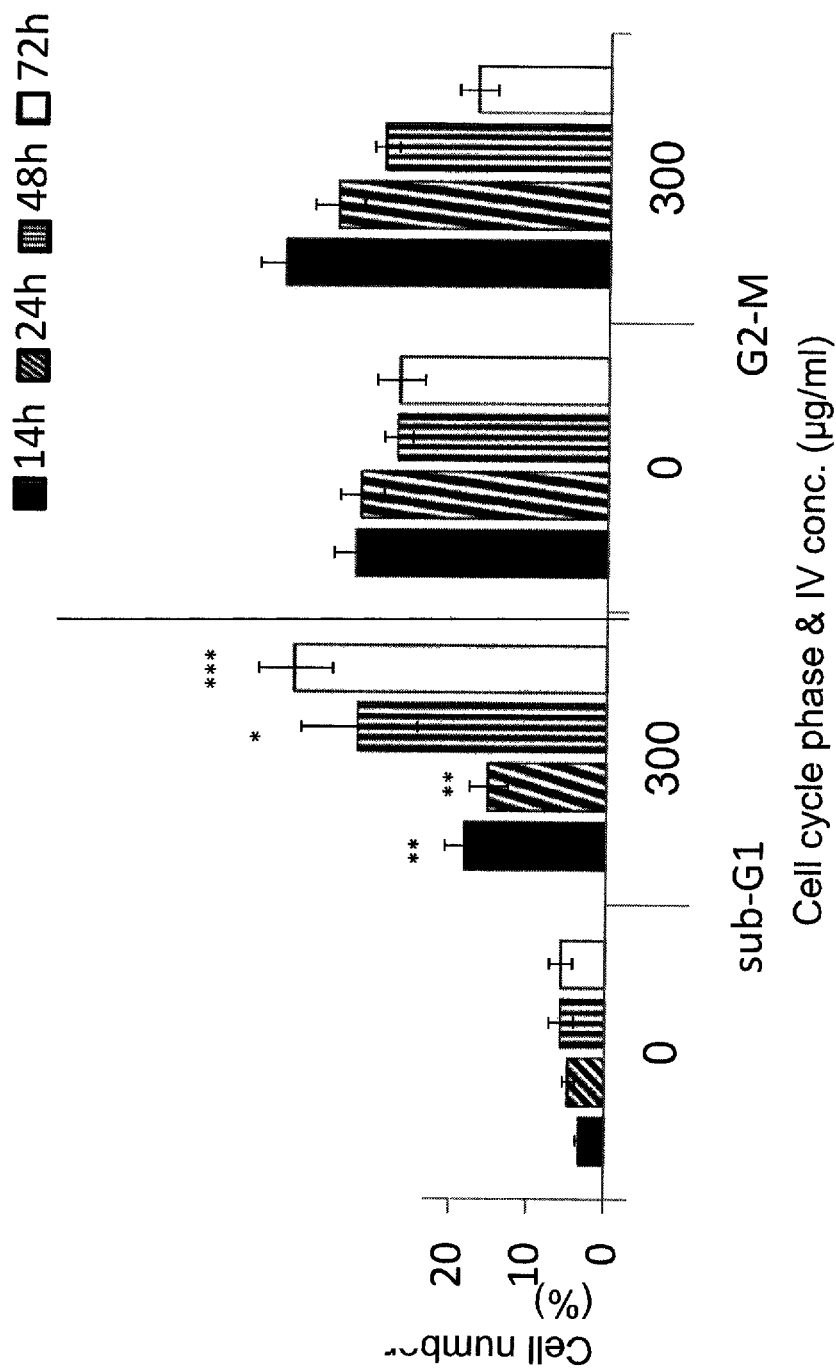
FIG. 8. Summary of percentage of cells in sub-G1 and G2/M phase following treatment of Colo320 with *Inula viscosa* extract using FACS analysis.
Figure 9A:
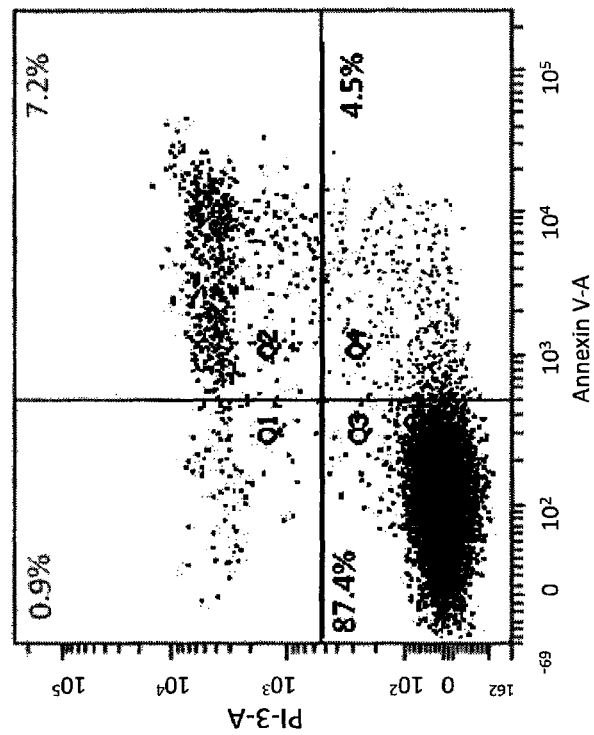
FIG. 9. Apoptotic effect of *Inula viscosa* extract on HCT116 cells. The lower left quadrant (Q3) corresponds to viable cells; the lower right quadrant (Q4) corresponds to early-apoptotic (annexin positive), cells the upper right (Q2) quadrant are late apoptotic cells (PI and Annexin positive) and upper left (Q1) quadrants corresponds to dead cells (PI positive).
Figure 9B:
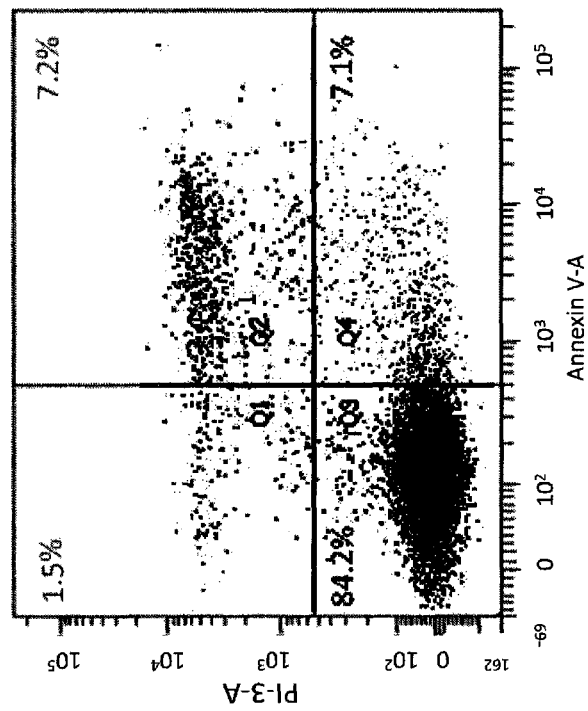
Figure 9E:
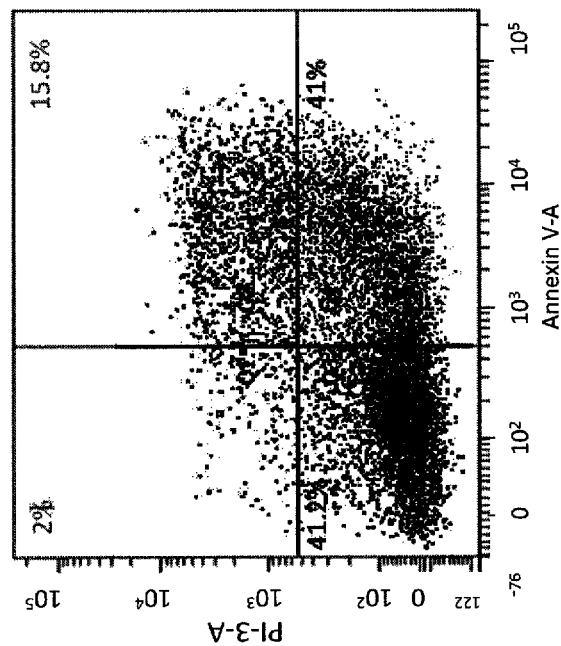
Figure 9D:
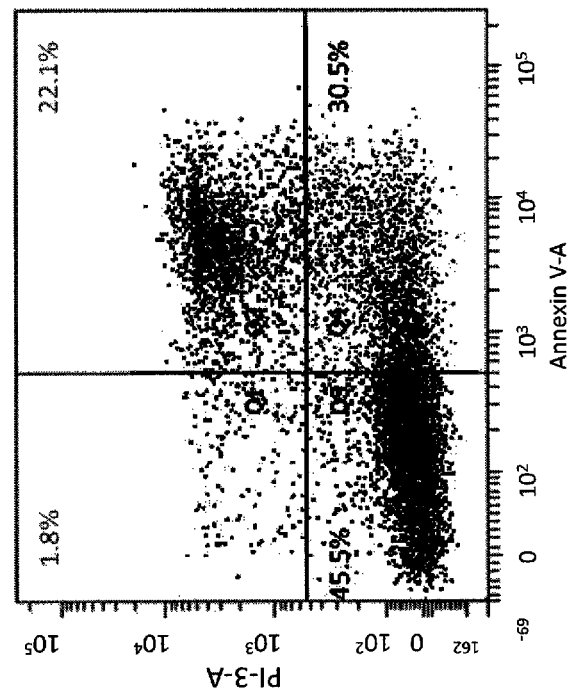

Flow cytometry revealed that exposure of HCT116, Colo320, and MC38 cells to 300 µg of IV extract exerted effects on the cell cycle distribution in a time dependent manner. The exposure of HCT116 cells to IV extract resulted in an increased proportion of cells in the G2/M phase (FIGS. 5-6) after 14 hr and 24 hr of treatment, as compared with the untreated cells (control). Moreover, extended period of treatment (48 and 72 hr) caused cells to exit from G2/M phase towards the sub-G1 phase, indicating apoptotic cell death. Following 24, 48 and 72 hr of IV treatment there was a significant increase in cell number in the sub-G1 phase (apoptotic phase) ($P<0.01$, $P<0.001$, $P<0.001$, respectively). Meaning that 9.74±1.76%, 29.7±5.62% and 48.47±5.67% of the cells are apoptotic after 24, 48 and 72 hr of 300 µg/ml IV treatments, respectively—approximately increased to 3, 6 and 9 folds compared with control. FIGS. 7-8 and 28-29 show similar results obtained using HCT116 and MC38, respectively.

Quantification of Apoptotic Cells by Annexin V-FITC

HCT116, Colo320 and MC38 cells ($2\times10^5$) were seeded in flasks having surface area of 25 cm$^2$ and allow to attach overnight. The cells were treated with 300 µg/ml IV extract for 14, 24, 48 or 72 hours. To detect early and late apoptosis, both adherent and floating cells were harvested together. Treated and untreated cells were harvested by trypsinization, washed and suspended in ice-cold PBS. The washed cell pellet was resuspended in ice-cold binding buffer containing FITC-conjugated annexin V and PI. The samples were incubated at room temperature for 15 min in the dark before analysis by flow cytometer (BD FACSCanto II) and managed with FACSDiva software.

Figure 10:
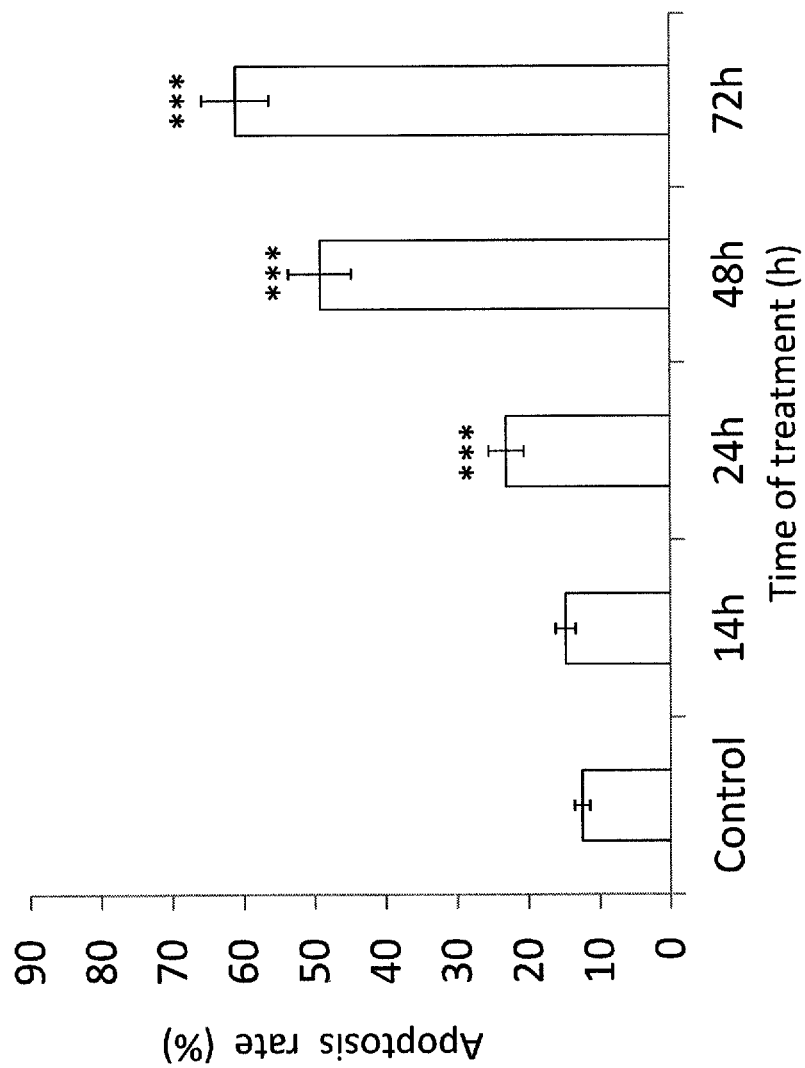
FIG. 10. Summary of percentage of apoptotic cells induction by *Inula Viscosa* extract in HCT116 as determined by Annexin V and PI.

In control untreated HCT116 cells, apoptosis rate was determined to be about 12%. Within 24 hours of incubation with IV extract, significant increase (to about 22%) in apoptosis rate was detected. Apoptosis rates upon 48 and 72 hours of incubation increased to about 50% and 65% respectively (FIGS. 9 and 10).

Figure 11:
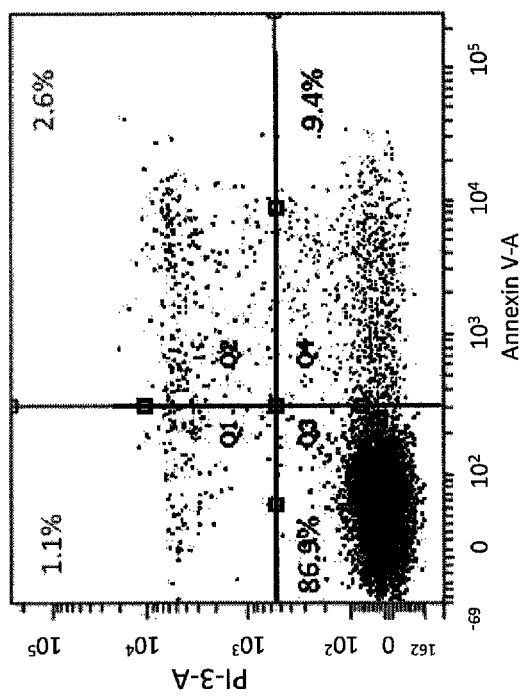
FIG. 11. Representative results for the apoptotic effect of *Inula viscosa* extract on Colo320 cells. Treated (B-E) and untreated (A) cells were harvested, washed, stained with Annexin V-FITC and propidium iodide (PI) and analyzed by flow cytometry. Annexin V staining is represented on the x-axis and PI staining is represented on the y-axis. The lower left quadrant (Q3) corresponds to viable cells; the lower right quadrant (Q4) corresponds to early-apoptotic (annexin positive), cells the upper right (Q2) quadrant are late apoptotic cells (PI and Annexin positive) and upper left (Q1) quadrants corresponds to dead cells (PI positive).
Figure 11:
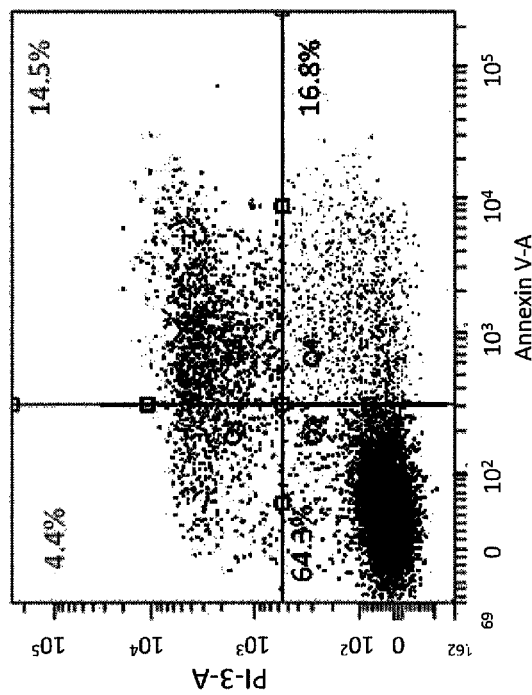
Figure 11:
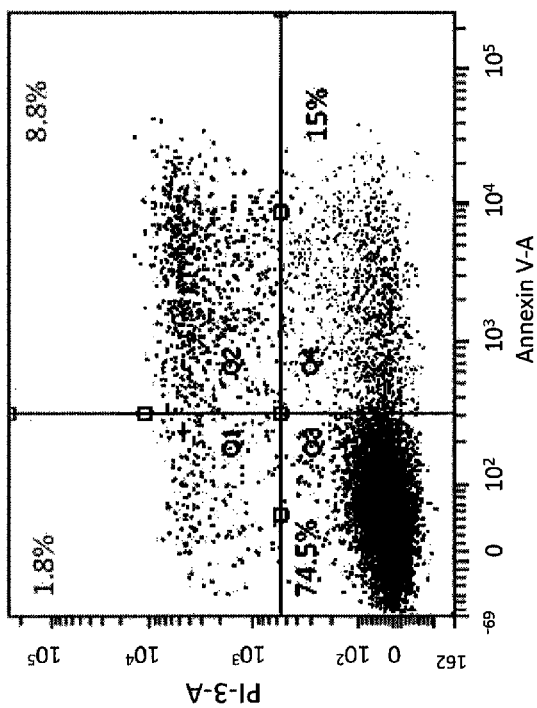
Figure 12:
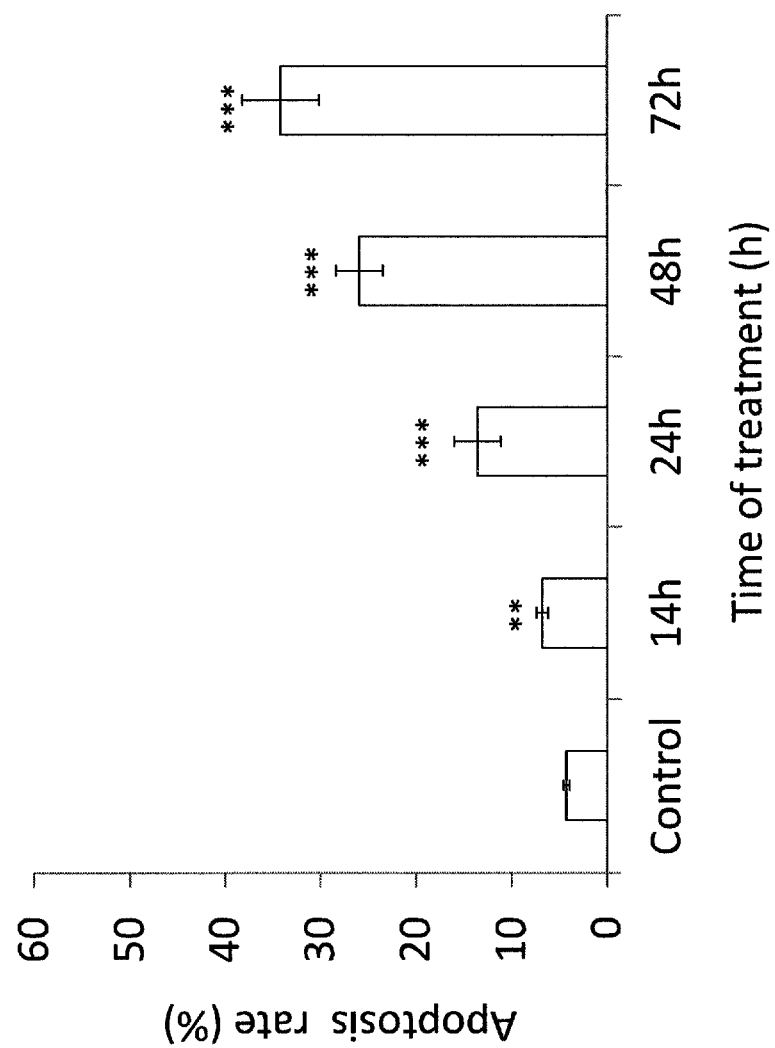
FIG. 12. Summary of apoptotic cells inducted by *Inula Viscosa* extract in Colo320 as determined by Annexin V and PI.
Figure 13B:
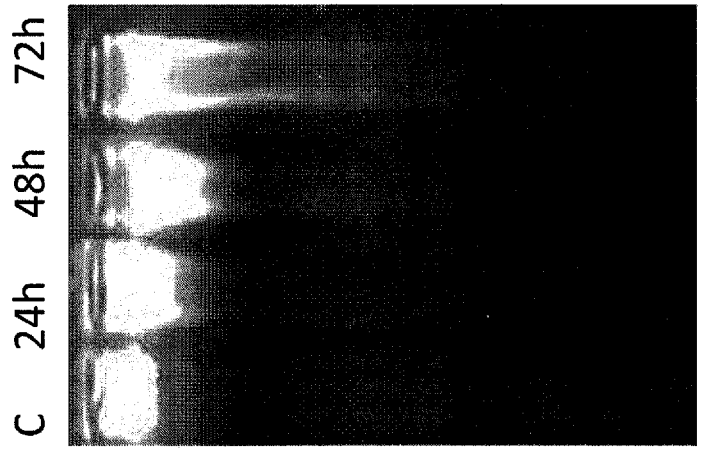
FIGS. 13A-B. Agarose gel electrophoresis of DNA extracted from HCT116 (13A) and Colo320 (13B) cells after treatment with *Inula viscosa* extract.
Figure 13A:
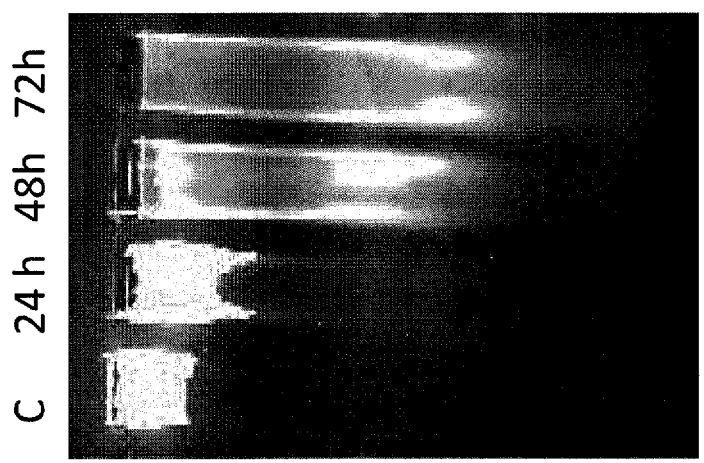

In control untreated Colo320 cells, apoptosis rate was determined to be about 4% (FIG. 11). Within 14 hours of incubation with IV extract, significant increase (to about 8%) in apoptosis rate was detected. Apoptosis rates upon 24, 48 and 72 hours of incubation increased to 15%, 25% and about 35% respectively (FIG. 12).

Figure 30A:
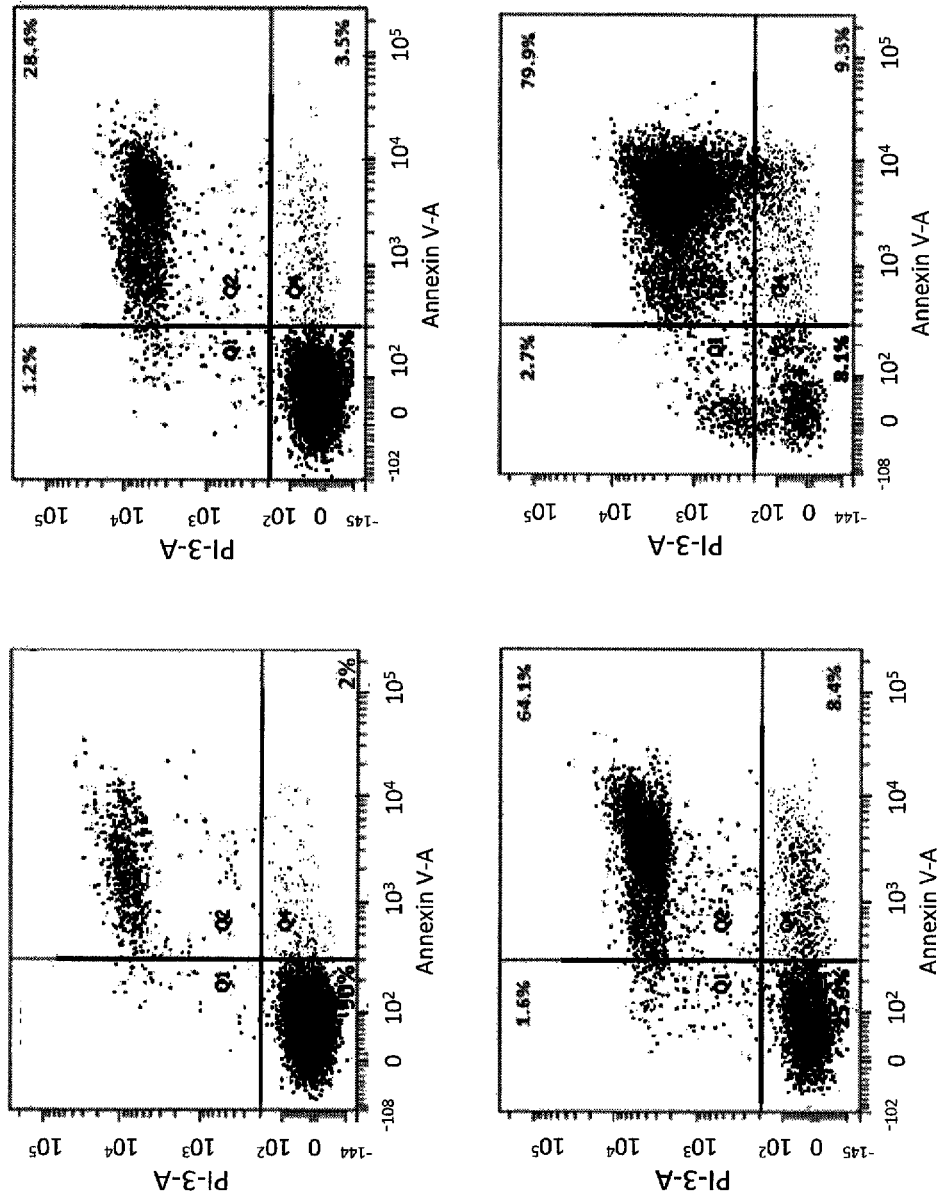
FIGS. 30A-B. Apoptotic effect of *Inula viscosa* extract on MC38 cells. (30A) Representative results, showing the distribution of cells. Annexin V staining is represented on the x-axis and PI staining is represented on the y-axis. The lower left quadrant (Q3) corresponds to viable cells; the lower right quadrant (Q4) corresponds to early-apoptotic (annexin positive), cells the upper right (Q2) quadrant are late apoptotic cells (PI and Annexin positive) and upper left (Q1) quadrants corresponds to dead cells (PI positive). (30B) Summary of percentage of apoptotic cells induction by *Inula Viscosa* extract as determined by Annexin V and PI.
Figure 30B:
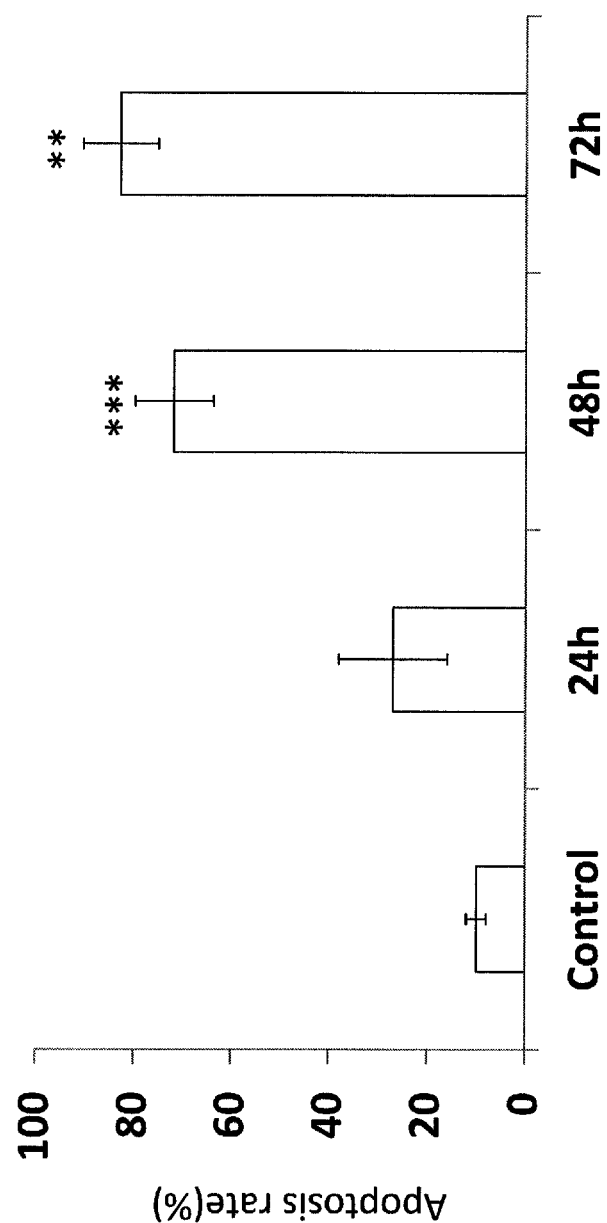

In control untreated MC38 cells, apoptosis rate was determined to be about 10%. Within 24 hours of incubation with IV extract, an increase (to about 26%) in apoptosis rate was detected. Apoptosis rates upon 48 and 72 hours of incubation increased significantly to 73% and about 82% respectively (FIG. 30).

Apoptosis Induced by IV Extract-Detection by TUNEL Assay

Figure 14A:
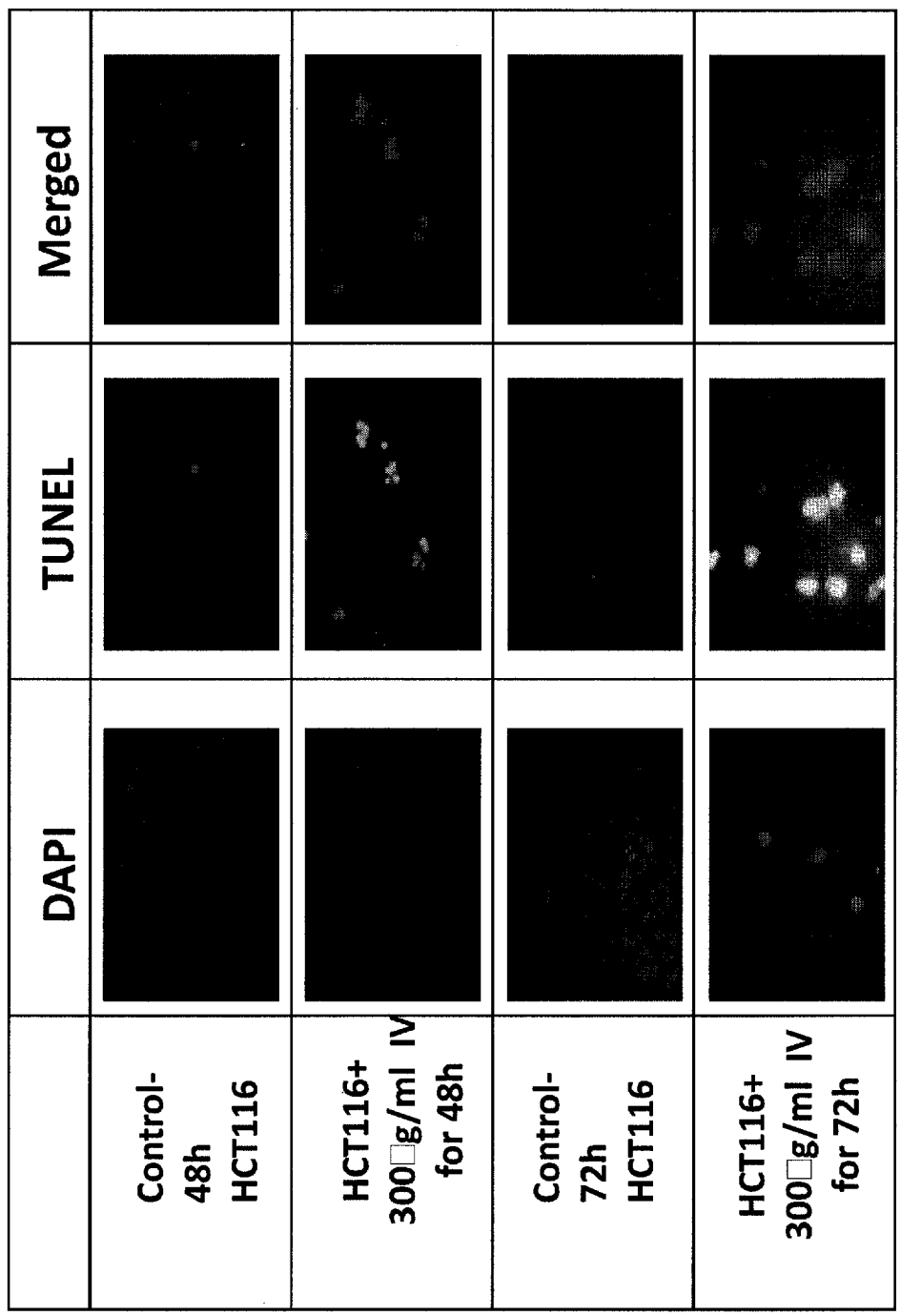
FIGS. 14A-B. Effect of *Inula viscosa* extract on the induction of apoptosis in HCT116 (14A) and Colo320 (14B) cells analyzed by DAPI and TUNEL staining. The TUNEL positive (shining orange) cells are apoptotic cells, nuclei are labeled with DAPI (blue) and merge between DAPI and TUNEL appears pink. Cells were visualized by fluorescence microscopy.
Figure 14B:
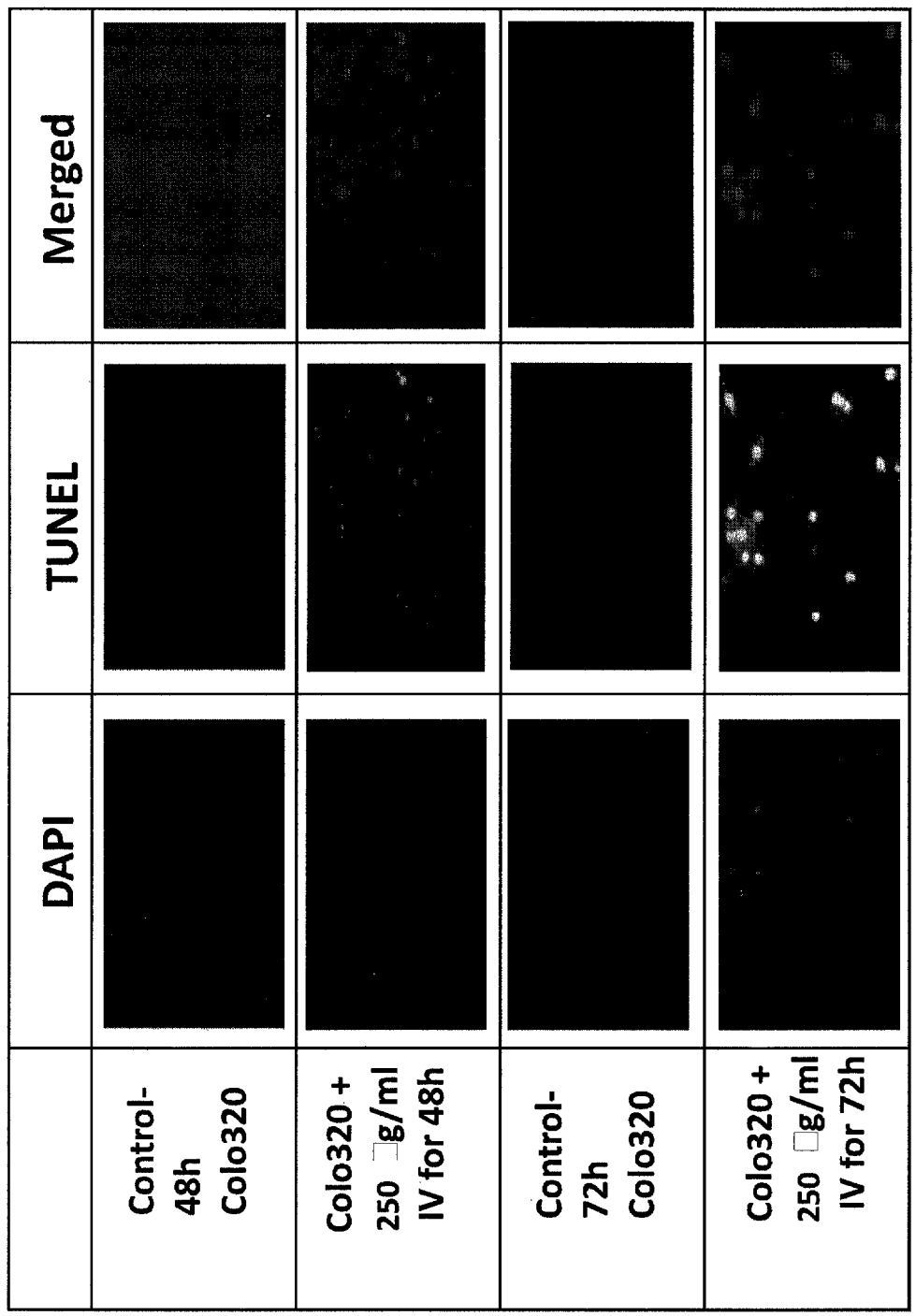
Figure 15A:
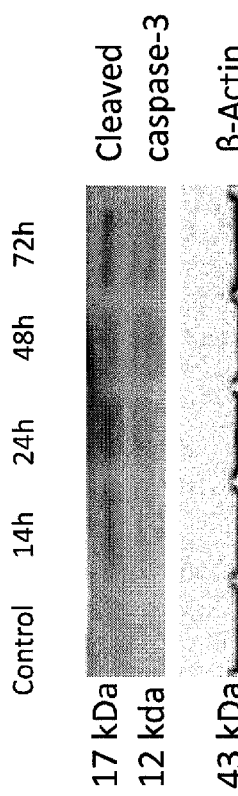
FIGS. 15A-C. Western blot analysis on the expression levels of procaspas-3 and activated caspase-3 following treatment of HCT116 cells with *Inula viscosa* extract. (15A) Western blotting results; upper bands, uncleaved caspase-3, middle bands, activated caspase-3 and lower bands are -actin. 15B-C: Average expression levels of procaspase-3 (15B) and cleaved caspase-3 (15C); density values were calculated as a control from the proper -actin and as a percent of control.
Figure 15B:
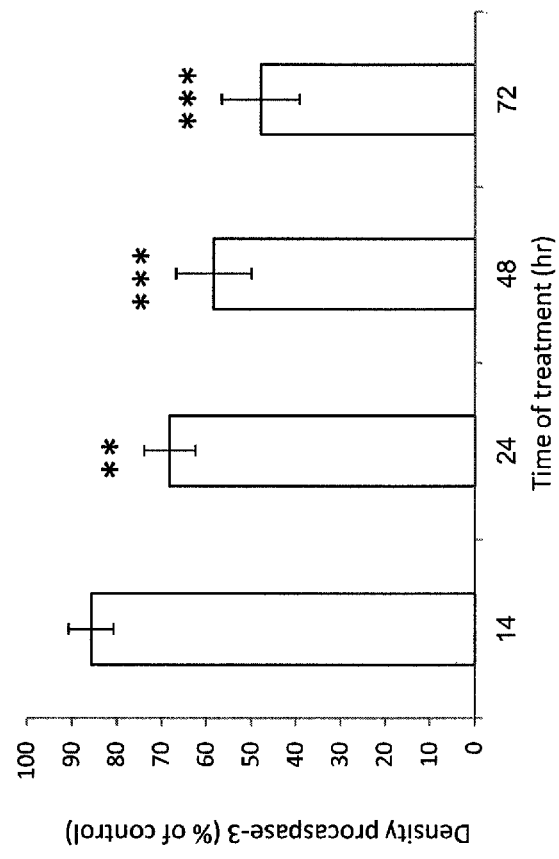
Figure 15C:
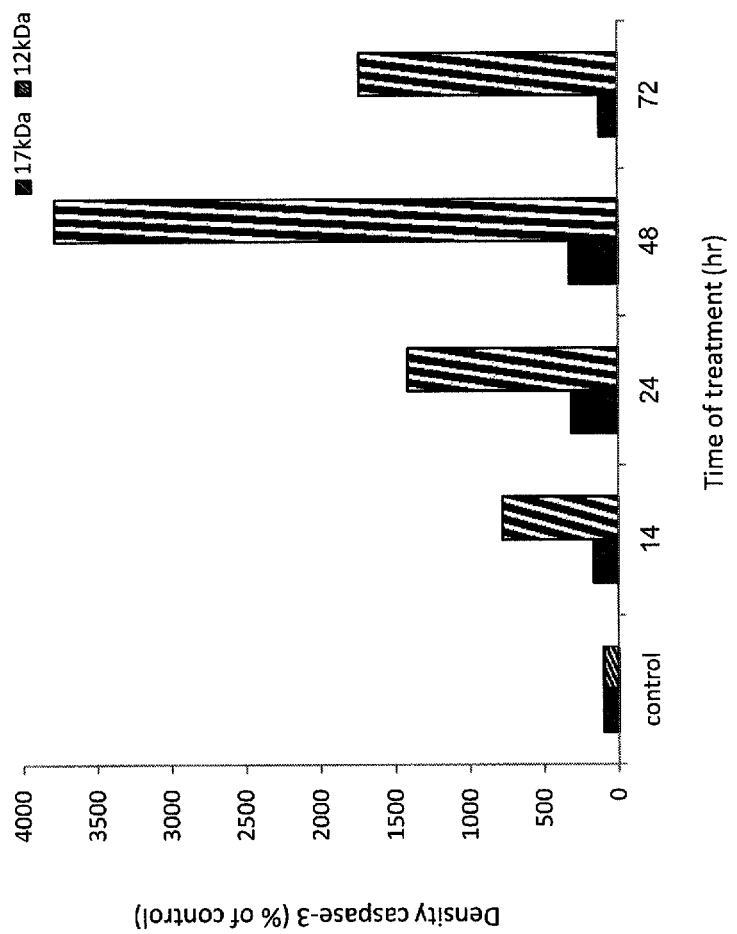
Figure 16A:
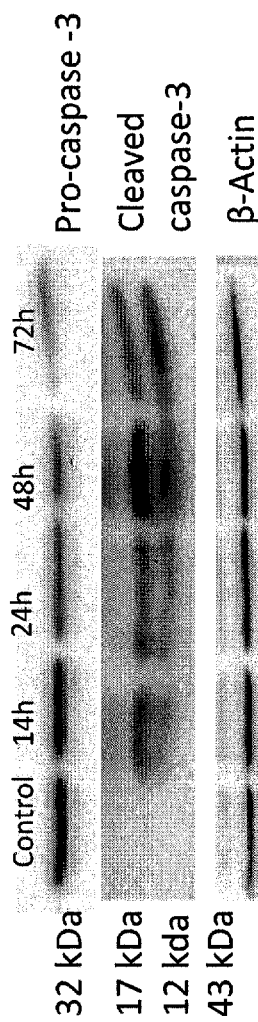
FIGS. 16A-C. Western blot analysis on the expression levels of procaspas-3 and activated caspase-3 following treatment of Colo320 cells with *Inula viscosa* extract. 16A: Western blotting results; upper bands, uncleaved caspase-3, middle bands, activated caspase-3 and lower bands are -actin. 16B-C: Average expression levels of procaspase-3 (16B) and cleaved caspase-3 (16C); density values were calculated as a control from the proper -actin and as a percent of control.
Figure 16B:
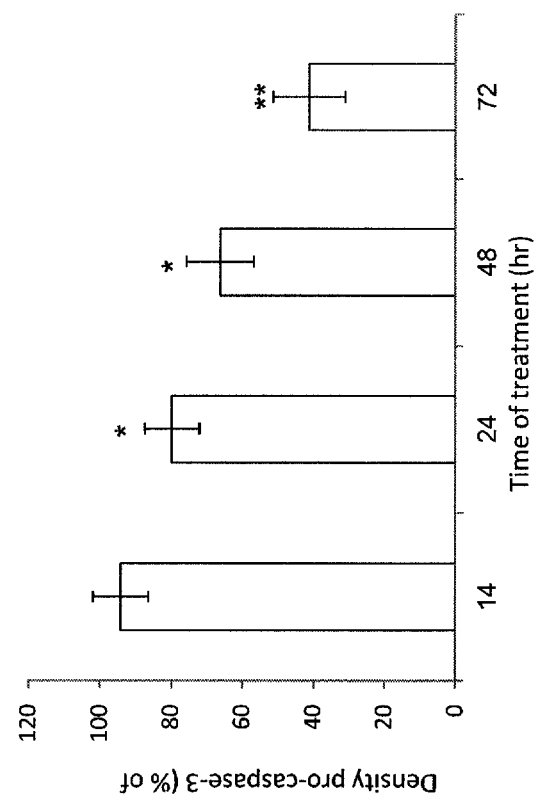
Figure 16C:
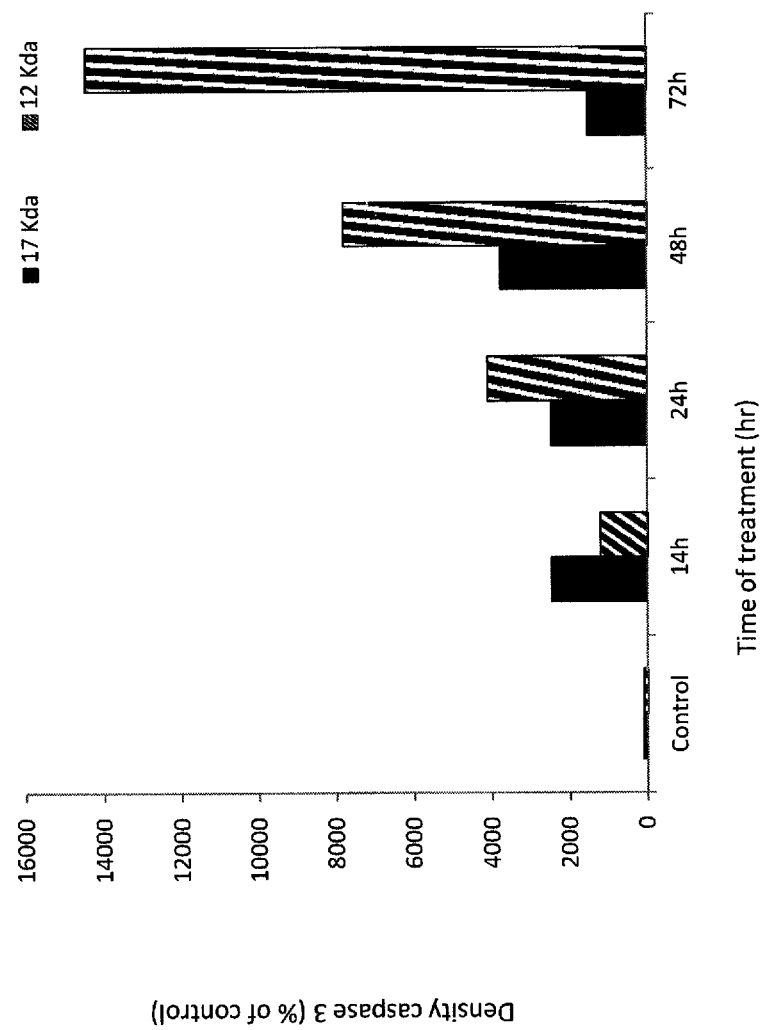
Figure 17A:
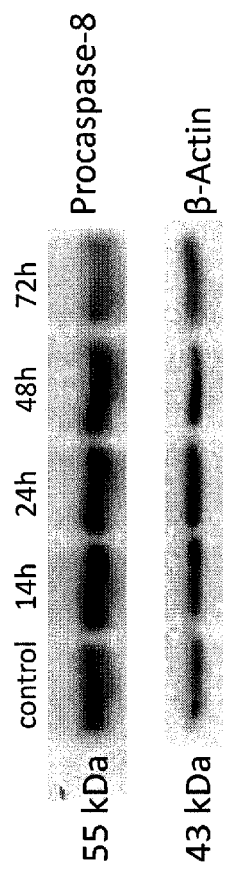
FIGS. 17A-B. Western blot analysis on the expression levels of procaspas-8 following treatment of HCT116 cells with *Inula viscosa* extract. 17A: Western blotting results; upper bands, uncleaved caspase-8 and lower bands are -actin. The figures shown are representative of three independent experiments. 17B: Average expression levels of procaspase-8; density values were calculated as a control from the proper -actin and as a percent of control.
Figure 17B:
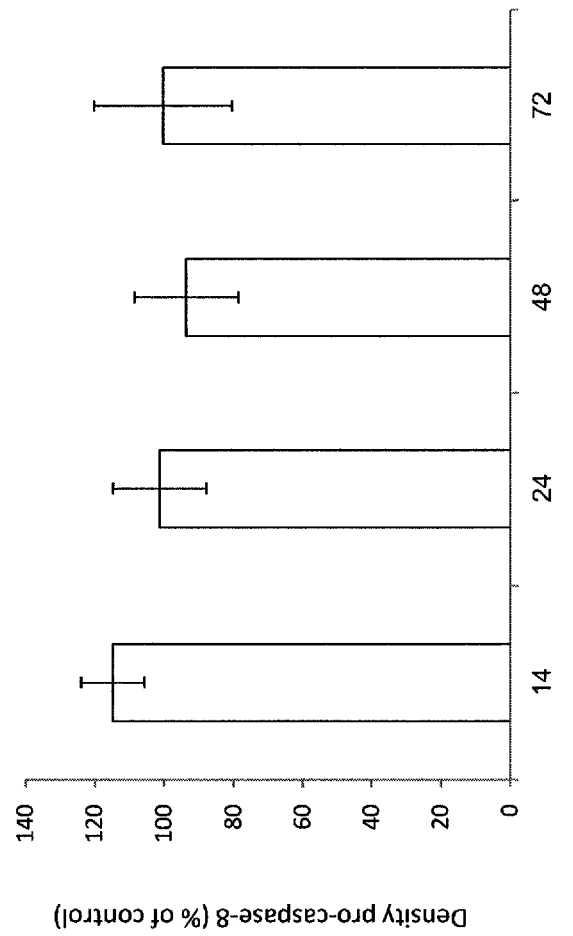
Figure 18C:
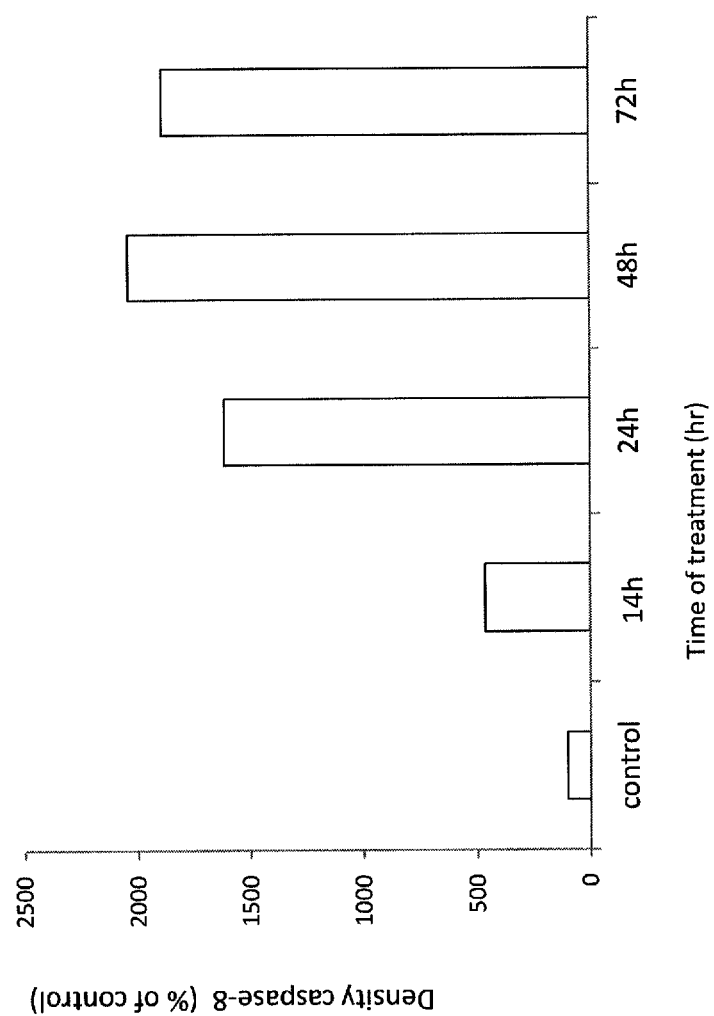
Figure 19C:
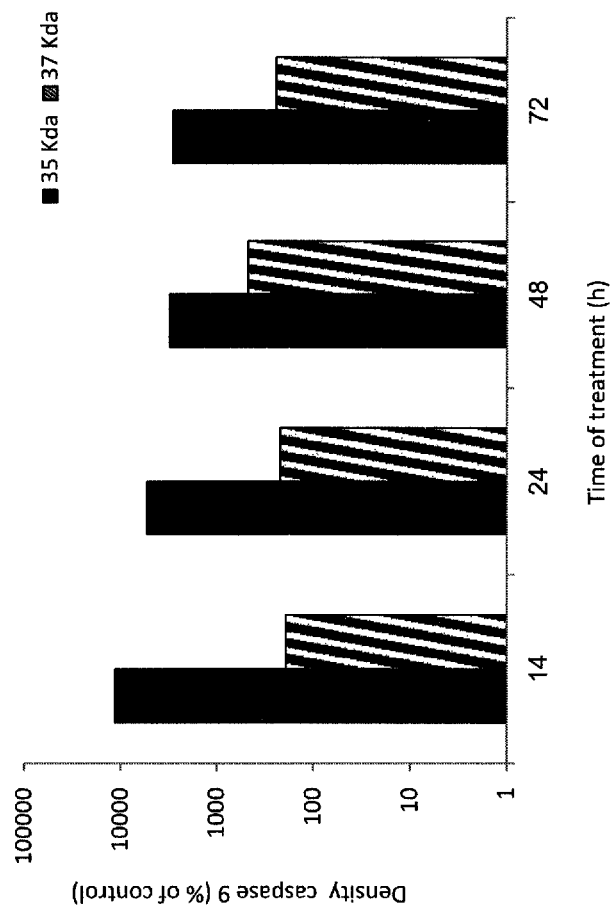
Figure 20A:
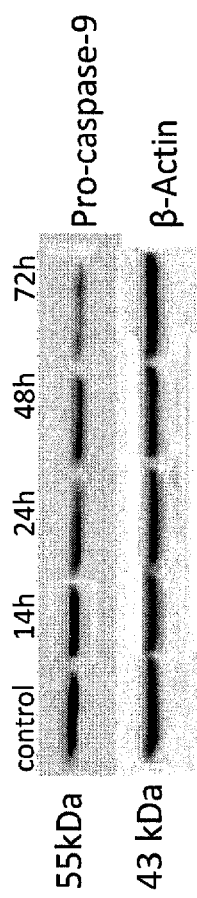
FIGS. 20A-B. Western blot analysis on the expression levels of procaspas-9 following treatment of colo320 cells with *Inula viscosa* extract. 20A: Western blotting results; upper bands, uncleaved caspase-9 and lower bands are -actin. 20B: Average expression levels of procaspase-8; density values were calculated as a control from the proper -actin and as a percent of control.
Figure 20B:
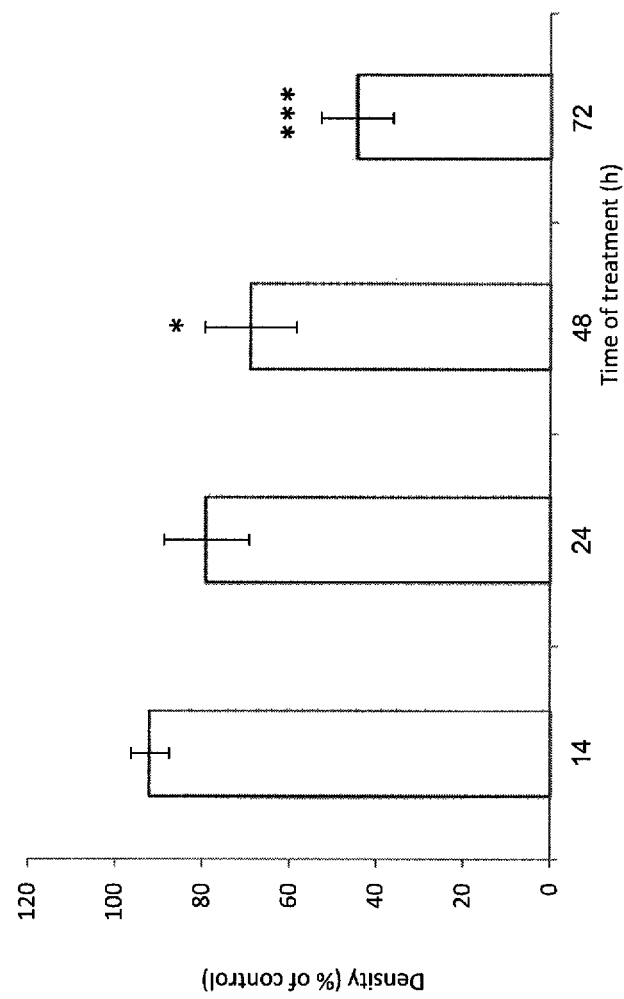
Figure 21A:
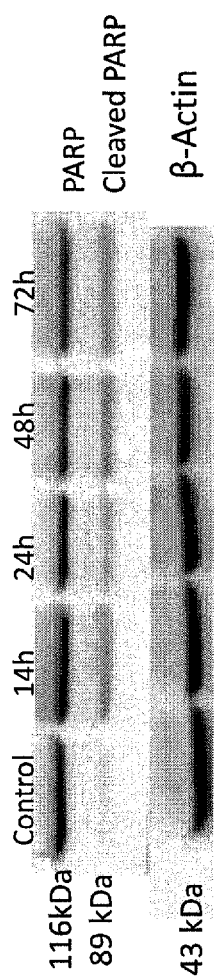
FIG. 21. Western blot analysis on the expression levels of PARP cleavage following treatment of HCT116 cells with *Inula viscosa* extract. 21A: Western blotting results; upper bands, uncleaved PARP (116 kDa), middle bands, cleaved PARP (89 kDa) and lower bands are -actin. 21B: Average expression levels of PARP and cleaved PARP; density values were calculated as a control from the proper -actin and as a percent of control.
Figure 21B:
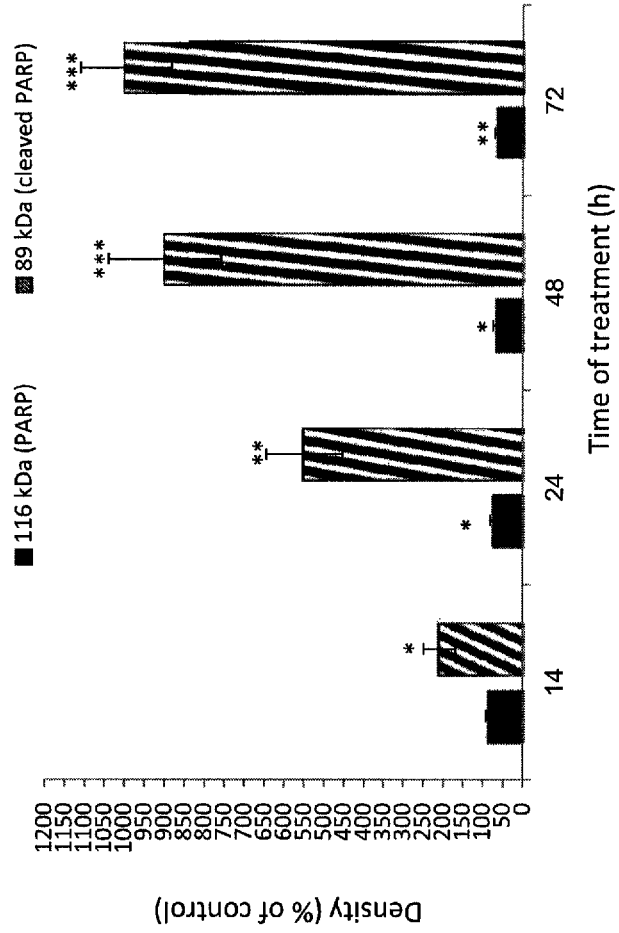
Figure 22A:
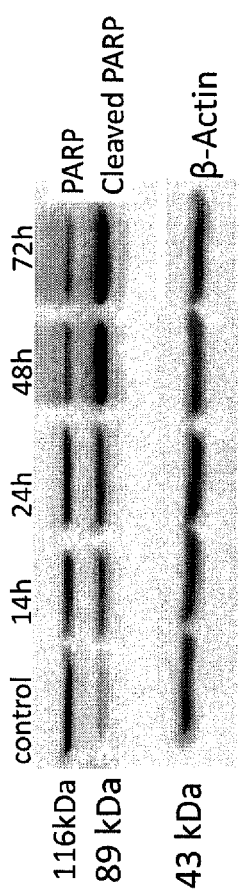
FIGS. 22A-B. Western blot analysis on the expression levels of PARP cleavage following treatment of Colo320 cells with *Inula viscosa* extract. 22A: Western blotting results; upper bands, uncleaved PARP (116 kDa), middle bands, cleaved PARP (89 kDa) and lower bands are -actin. 22B: Average expression levels of PARP and cleaved PARP; density values were calculated as a control from the proper -actin and as a percent of control.
Figure 22B:
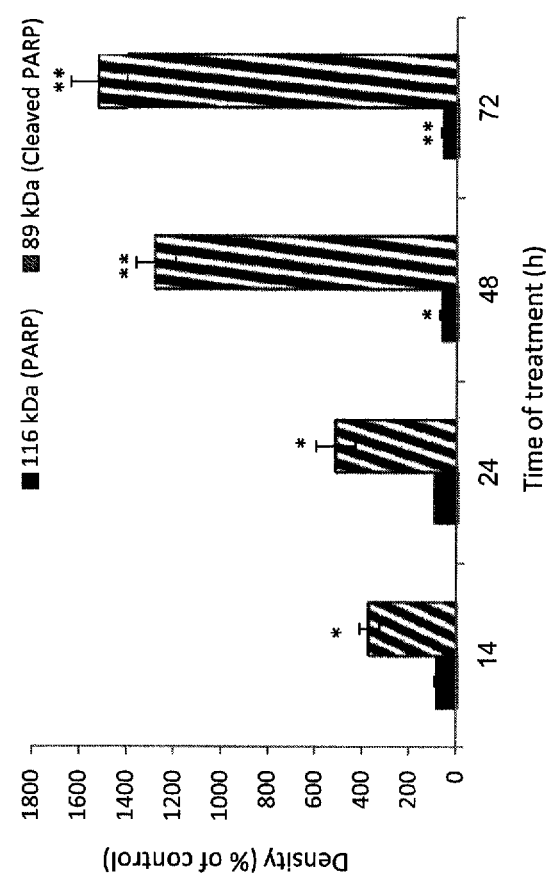

In order to confirm the apoptotic response as observed by Annexin V-FITC and DNA fragmentation on agarose gel electrophoresis assays, DAPI and TUNEL staining were preformed. HCT116 and Colo320 cell lines were grown in the absence or presence of 300 µg/ml of IV extract for 48 and 72 hr. As shown in FIG. 14A-B, extensive DNA fragmentation was visible by fluorescence microscopy in cells treated with IV, causing the appearance of a fluorescent orange color. While untreated cells (control) were negative to TUNEL staining, most of HCT116 (FIG. 14A) and Colo320 (FIG. 14B) cells treated with 300 µg/ml of IV extract were positive for apoptosis after 48 and 72 hr of treatment. Moreover, according to DAPI staining results, differences in the morphology of untreated cells' and the treated cells' nuclei can be observed in both cell lines (FIGS. 14A-B); IV-treated cells' nuclei appear to be more condensed (greater intensity of stain), while untreated cells' nuclei are large and un-condensed.

Figure 31:
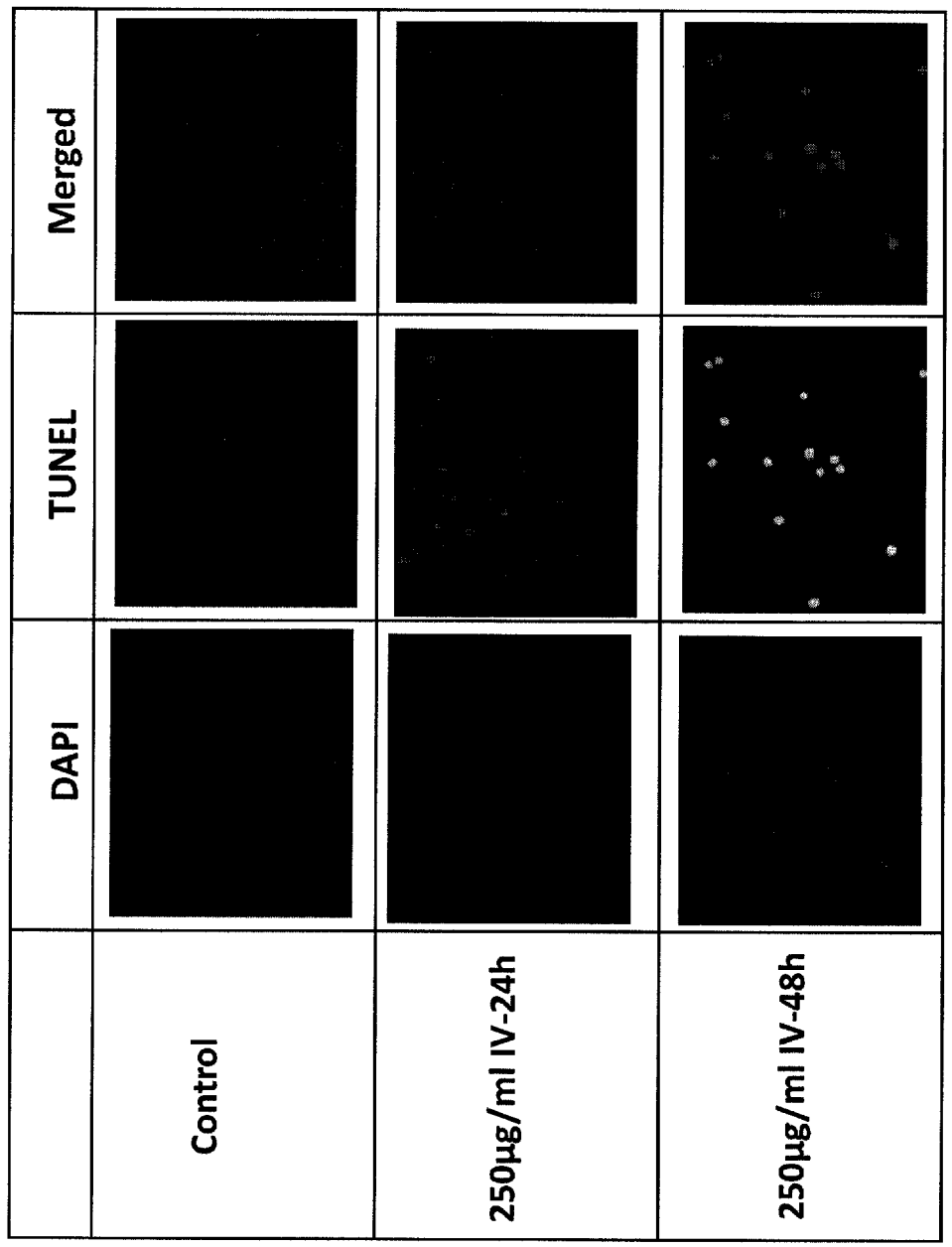
FIG. 31. Effect of *Inula viscosa* extract on the induction of apoptosis in MC38 cells analyzed by DAPI and TUNEL staining.

FIG. 31 shows similar results obtained when using MC38 cells grown in the absence and presence of 250 µg/ml of IV extract for 24 and 48 hr. While untreated cells (control) were negative to TUNEL staining, most of the IV extract-treated cells were positive for apoptosis after only 24 hr. Moreover, after 48 hr of IV treatment all the cells undergo apoptosis.

Figure 23A:
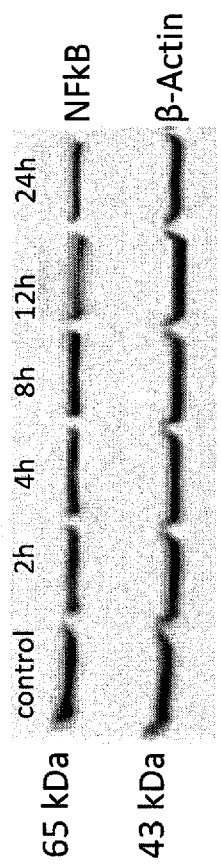
FIGS. 23A-B. Western blot analysis on the expression levels of p65, subunit of NFkB following treatment of HCT116 cells with *Inula viscosa* extract. 23A: Western blotting results; upper bands, NFkB (65 kDa) and lower bands are -actin. 23B: Average expression levels of NFkB; density values were calculated as a control from the proper -actin and as a percent of control.
Figure 23B:
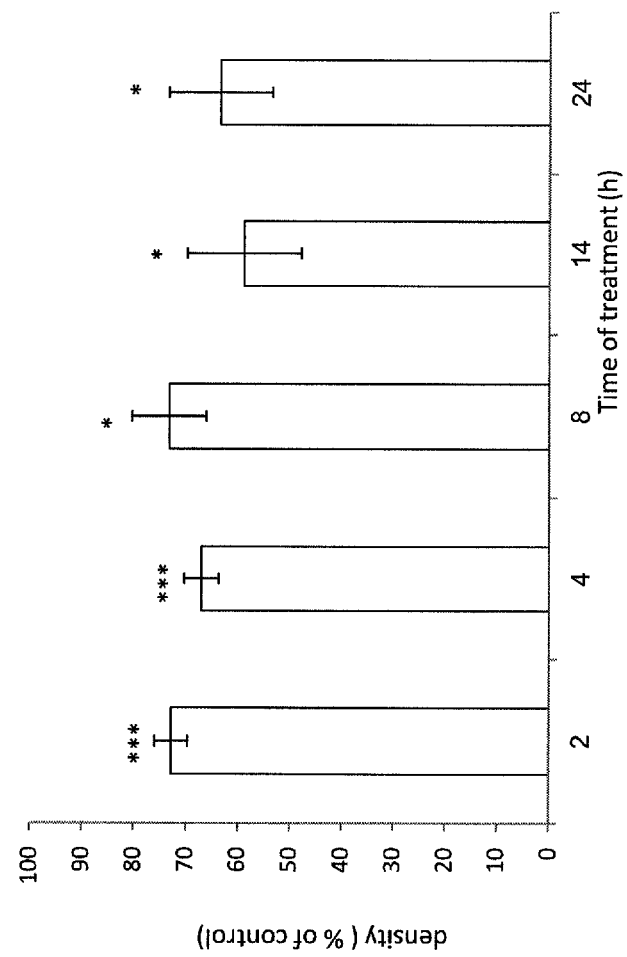
Figure 24A:
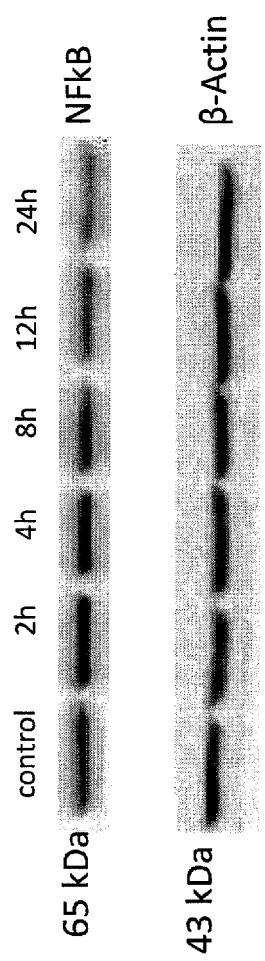
FIGS. 24A-B. Western blot analysis on the expression levels of NFkB following treatment of Colo320 cells with *Inula viscosa* extract. 24A: Western blotting results; upper bands, NFkB (65 kDa) and lower bands are -actin. The figures shown are representative of three independent experiments. 24B: Average Expression levels of NFkB; density values were calculated as a control from the proper -actin and as a percent of control.
Figure 24B:
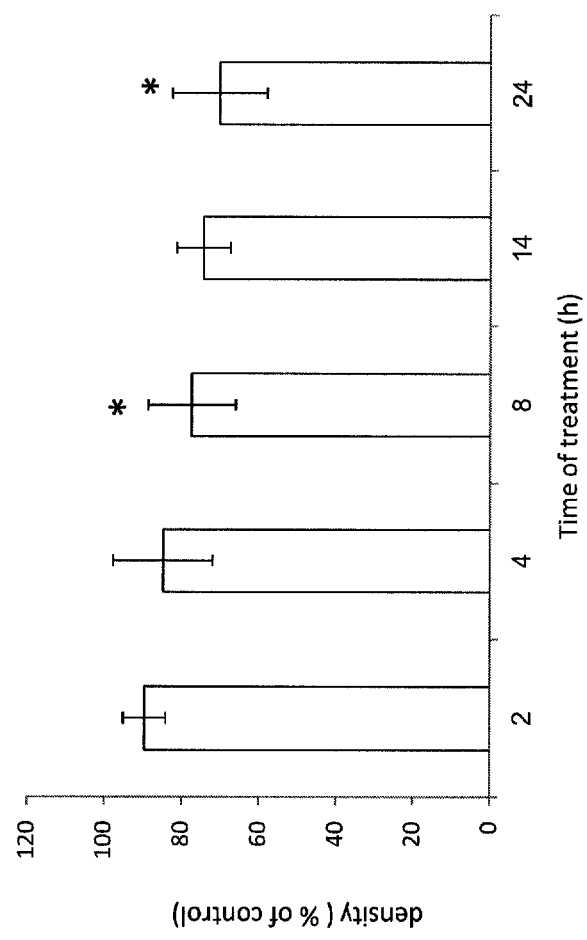

As shown above, the effective concentrations were found to be non-toxic to cells (FIGS. 4 and 27). Moreover, the induction of apoptosis was found to be through the intrinsic pathway on well differentiated cells (FIGS. 15, 17, 19 and 21) and through the intrinsic and extrinsic pathways in poorly differentiated cells (FIGS. 16, 18, 20 and 22). Moreover, it was found that the IV extract inactivated NF Kappa-B in both poorly and well differentiated cells (FIGS. 23-24).

Example 5

Effect of Treating Colon Cancer in Mice In Vivo

The therapeutic activity of IV extract as prepared in Example 1 was investigated in 6 week-old male C57BL/6 mice (20-25 gr. body weight) (Harlan Laboratories, Jerusalem, Israel). Mice were maintained in a standard cage (5 mice per cage) under sterile conditions; with air filter tops in a filtered laminar air flow room, at a temperature of 22° C. and were maintained at a 12 hour light/dark schedule. Rodent diet (Koffolk Inc., Tel-Aviv, Israel) and tap water were autoclaved and provided ad libitum. The mice were kept in the animal facility at least one week before starting the experiments. All in vivo experiments and procedures were approved by the Animal Ethics Committee at the Technion (Haifa, Israel).

MC38 (murine colon cancer) cells ($10^6$) were suspended in Dulbecco's modified eagle medium (DMEM, 0.2 ml) and were injected subcutaneously in to the right dorsal flank of the mice, using a 25-gauge needle (Terumo scientific Inc.) in order to induce tumor growth. When tumors were induced and the tumor size reached about 100 cubic millimeters (mm$^3$) (about 2 weeks after cell implantation), the animals were divided into 3 groups (n=8) based on the tumor size (control and treated groups). A fourth group included 8 control mice which were not injected with MC38 cells. The mice were treated by intraperitoneal (IP) injection with IV extract at 150 or 300 milligrams per kilogram of mouse weight (mg/kg) or with PBS (control groups). Treatments were conducted three times a week, during a three-week period and body weights and tumor volume were measured biweekly. Body weights were measured using a weighing scale (Precisa, Switzerland) and tumor volumes were measured with a digital caliper (Sylvac system, Switzerland) and calculated using the formula; length×width$^2$×0.52, where width represents the shortest dimension of the tumor. At the end of the treatment period, two mice from each group were taken to ultrasound imaging, and finally mice were sacrificed, tumors were surgically excised and their final weights and volumes were measured and tested for histological studies.

Figure 32A:
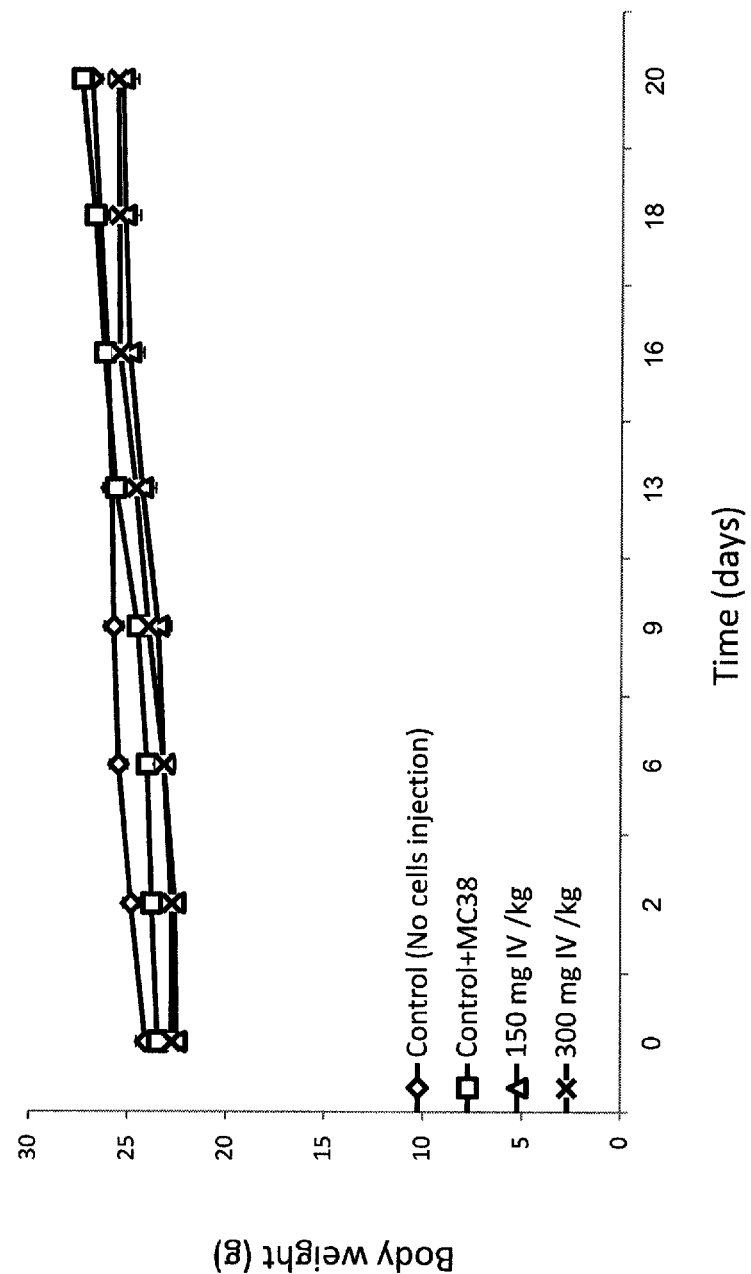
FIGS. 32A-B. Effect of IV extract on mice colon cancer cells (MC38) in C57BL/C mice on body weight (32A) and tumor volume (32B).
Figure 32B:
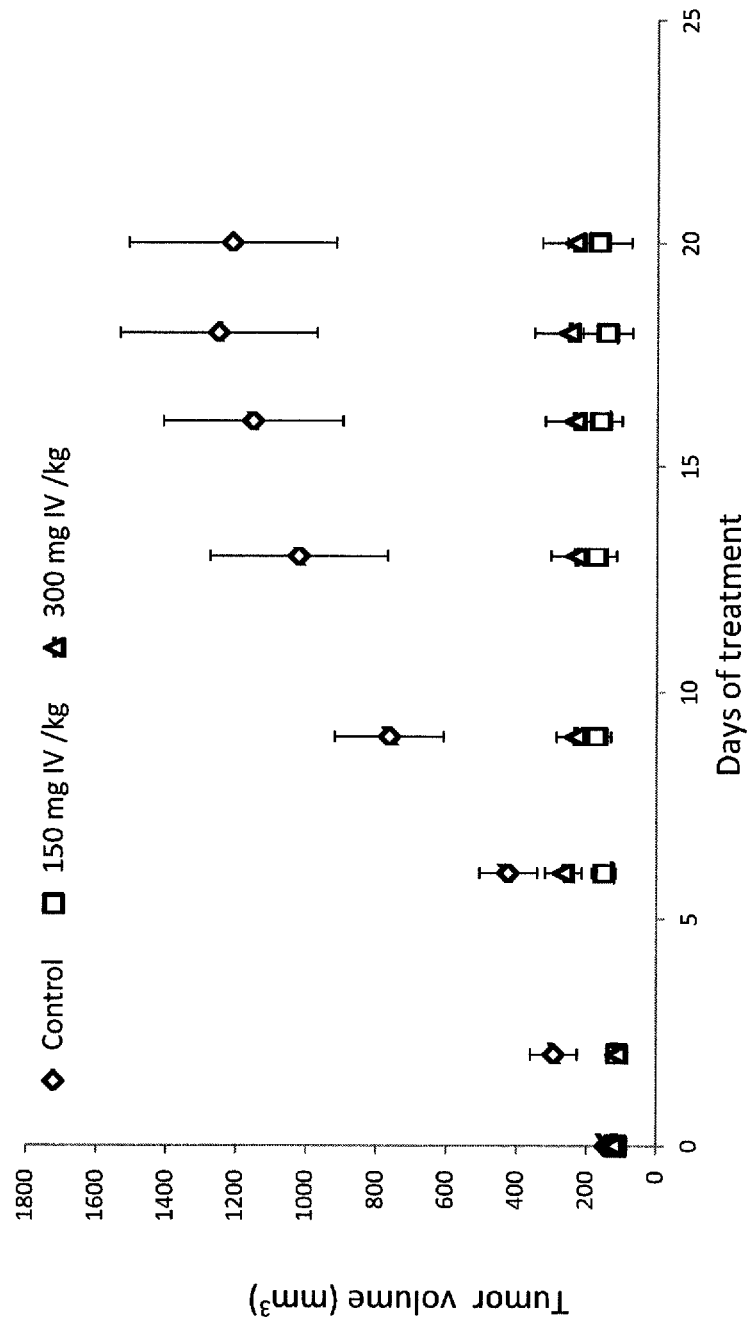

As shown in FIGS. 32A-B, tumor size grew in the vehicle-treated control group from the start of the treatment in the control group until 20 days. IV extract was successful in limiting tumor growth in both the group administered 150 mg/kg and in the group administered 300 mg/kg.

Figure 33A:
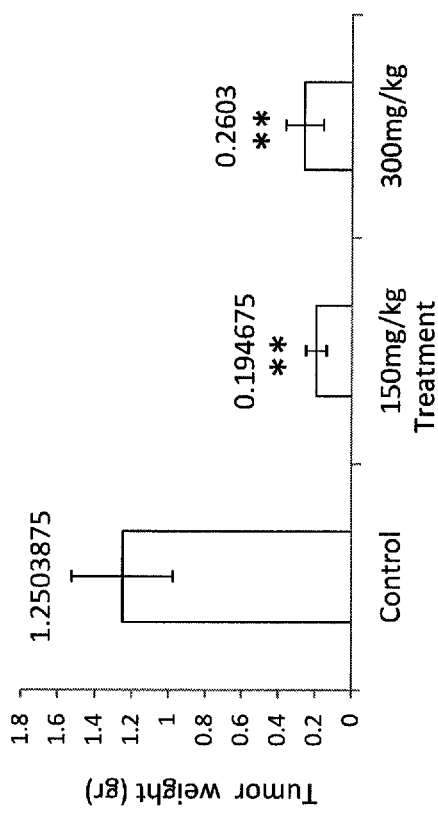
FIGS. 33A-B. Effect of *Inula viscosa* extract on final tumor weight (33A) and volume (33B).
Figure 33B:
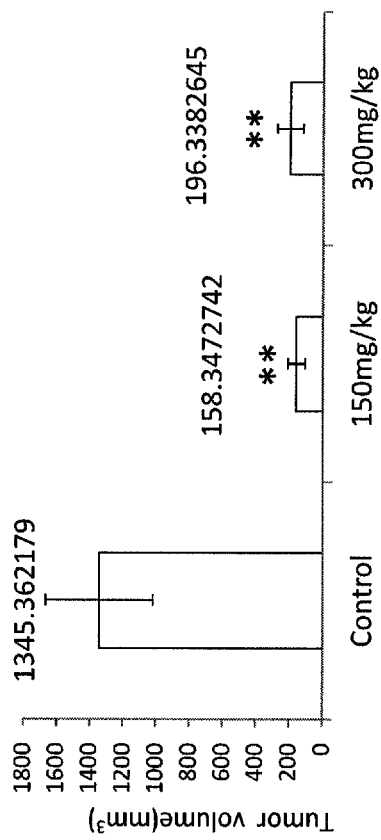
Figure 34:
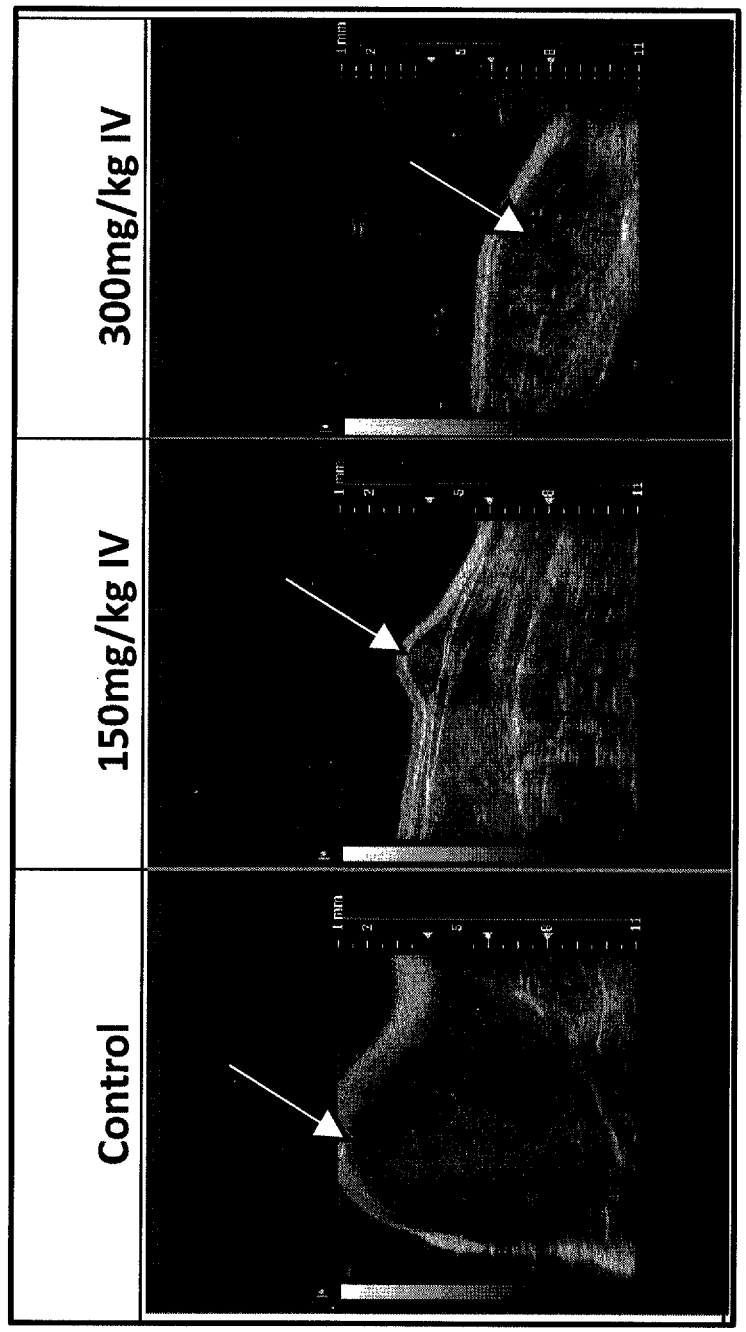
FIG. 34. Ultrasounds imaging of the tumors using.
Figure 35:
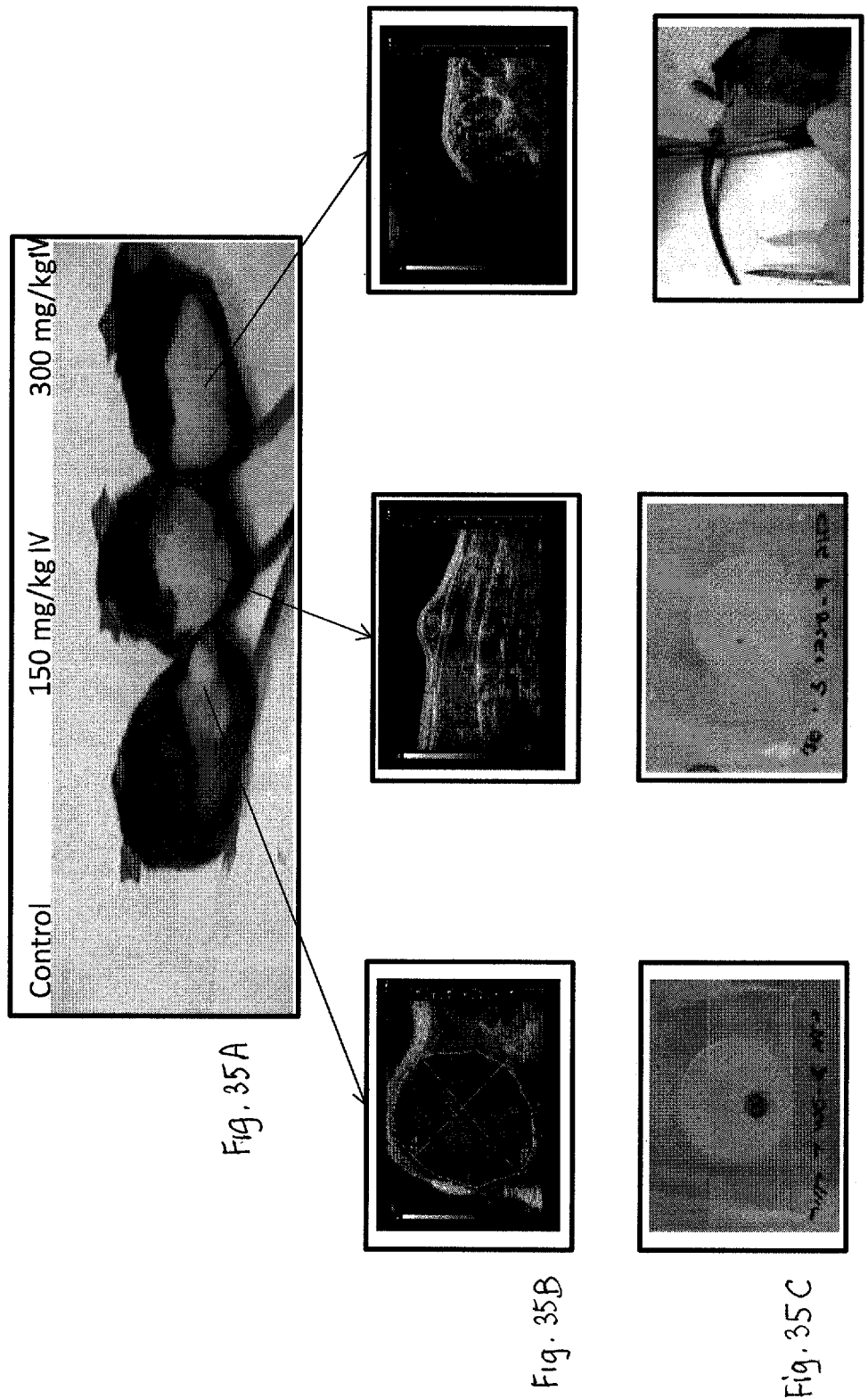
FIGS. 35A-C. Inhibition effect of *Inula viscosa* extract on tumor growth in vivo and in situ. At the end of the treatment period, mice were shaved (35A) using electric hair clipper followed by an application of depilatory cream to remove the fine hair and enhance the image quality, and in vivo tumor US has been done (35B). The round circles represent tumor measurement using software incorporated in to VEVO 2100 device. (35C) Pictures of the tumors collected at the end of treatment.
Figure 36:
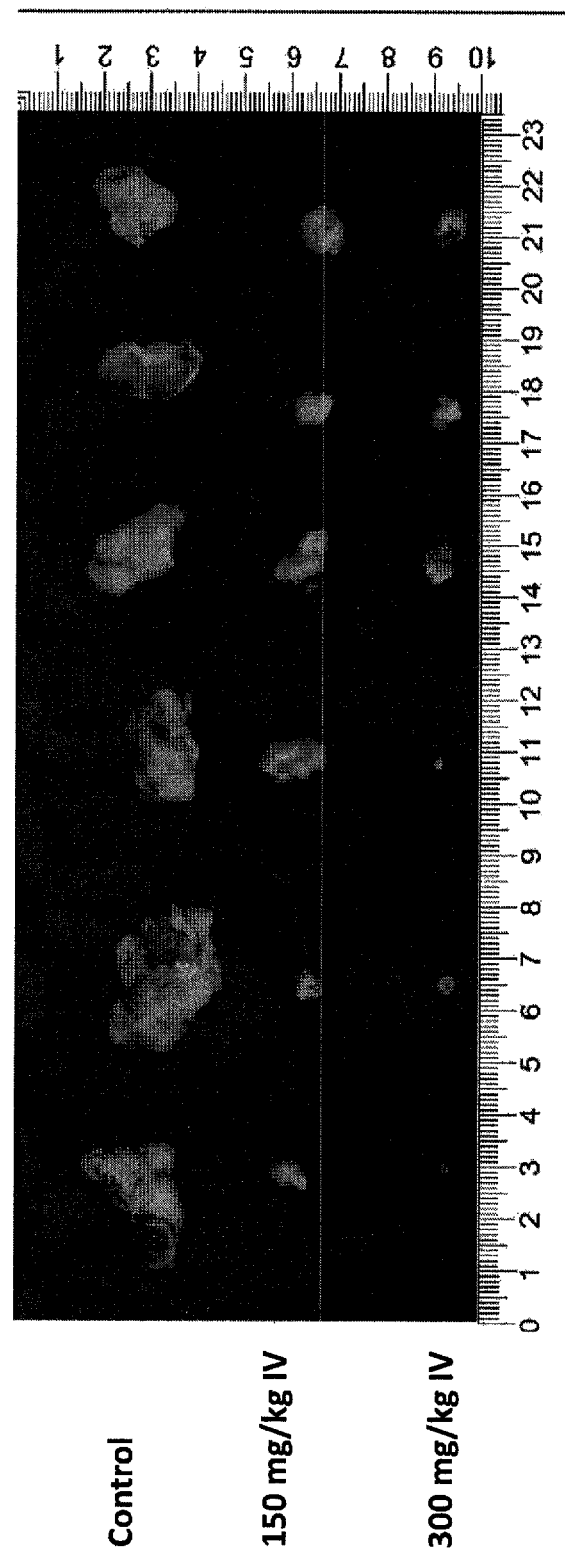
FIG. 36. Photograph of the tumors collected after 21-day *Inula viscose* treatment. At the end of the treatment period, mice were scarified, tumors were separated and a representative picture of the tumors from control or treated (150 or 300 mg IV extract per kg) groups was taken using a camera.

As shown in FIGS. 33A and 33B, tumor weight and tumor volume were significantly lower upon sacrifice in both treatment groups relative to the control group, indicating that IV extract is effective in treating cancer and limiting cancer growth in animals, in both the 150 and 300 mg/kg groups.

Although IV extract was administered to mice systemically, and not locally to the tumor, it was still effective in penetrating the afflicted organ and reducing tumor size without causing adverse side effects in the mice.

Blood samples were also collected from the mice for analysis of liver and kidney functioning. Treatment of the animals with two effective doses, 150 and 300 mg/kg, had no effect on kidney and liver functions indicating that that IV (even at the higher doses of 300 mg/kg) is not toxic to the animals (Table 2).

TABLE 2

Serum chemistry analysis from mice treated with *Inula viscosa* extract for 21-days

| Serum chemistry | Control (no cancer-Untreated) | Control (Untreated) | *Inula viscosa* treated 150 mg/kg | *Inula viscosa* treated 300 mg/kg | p-value (1) | p-value (2) |
|---|---|---|---|---|---|---|
| Kidney function | | | | | | |
| UREL (mg/dL) | 47 ± 3.78 | 55.6 ± 5.87 | 51.5 ± 2.13 | 48.7 ± 2.61 | 0.43 | 0.231 |
| NA-I (mmol/L) | 156.96 ± 8.95 | 152.32 ± 0.52 | 151.48 ± 1.39 | 151.23 ± 1.55 | 0.687 | 0.638 |
| CA (mg/dL) | 8.74 ± 0.55 | 11.15 ± 0.28 | 10.80 ± 0.19 | 10.5 ± 0.28 | 0.317 | 0.175 |
| K-I (mmol/L) | 14.64 ± 17.69 | 7.39 ± 0.62 | 9.09 ± 0.75 | 8.80 ± 0.69 | 0.167 | 0.217 |
| Creatinine (mg/dL) | <0.2 | <0.2 | <0.2 | <0.2 | | |
| Liver function | | | | | | |
| ALT (u/l) | 59.78 ± 9.39 | 99.28 ± 41.39 | 114.82 ± 63.53 | 67.48 ± 12.81 | 0.756 | 0.569 |
| ALP2L (U/L) | 64 ± 8.84 | 87 ± 3.86 | 85 ± 10.86 | 77.11 ± 6.29 | 0.865 | 0.206 |
| AST (U/L) | 323.94 ± 71.4 | 244.16 ± 64.4 | 269.30 ± 68.8 | 380.15 ± 87.3 | 0.803 | 0.309 |
| GGTI (U/L) | 6.9 ± 1.68 | 0.32 ± 0.25 | 1.28 ± 0.67 | 3.37 ± 2.92 | 0.331 | 0.486 |

Figure 37:
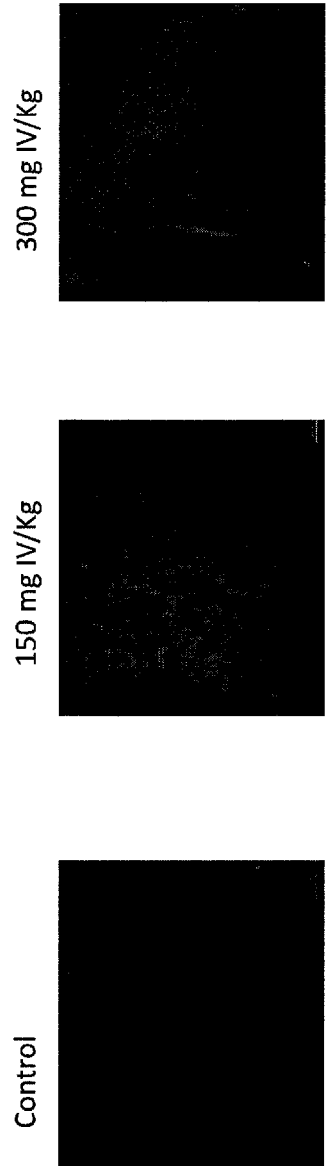
FIG. 37. DAPI and TUNEL staining of tumor sections. In order to explore apoptotic characteristics of the cells, 4 μm sections from the tumors were stained with DAPI and TUNEL and analyzed under a fluorescent microscopy (magnification, 200×).
Figure 38:
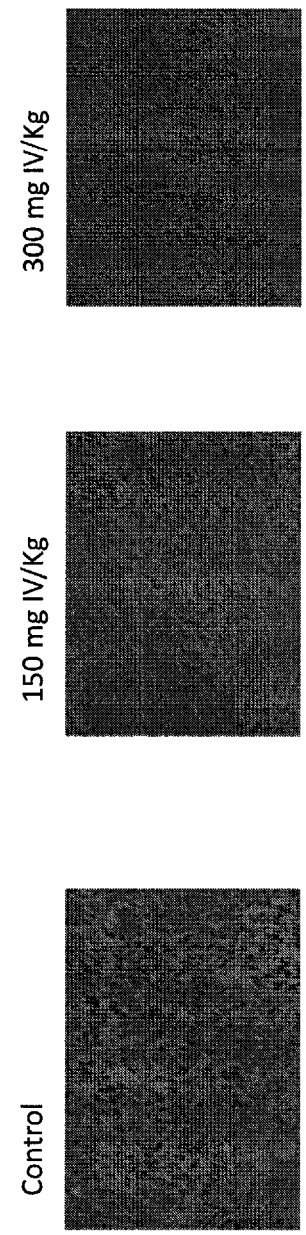
FIG. 38. Proliferation of cells from the tumors. In order to explore proliferation of the cells, slides from the tumor were incubated with a specific antibody as described under section 8.2. The figures shown are representatives of the results obtained (Magnification, 200×).

At sacrifice, tumors were excised and kept in formalin, and then paraffin blocks were prepared. Four micron sections were cut and fixed onto slides for Terminal deoxynucleotidyl transferase dUTP nick end labeling (TUNEL) assay and Ki-67 staining (FIGS. 37 and 38).

Paraffin-embedded sections of tumors were fixed in 4% parafomaldehyde and dewaxed. Slides were deparaffinized by heating at 60° C. for 1 hour in a hybridization oven (Thermo scientific Inc.). Next, slides were placed in a plastic slide holder and filled with W-CAP citrate buffer pH=6 (Bio-Optica Milano s.p.a). The slide holder was placed in a water bath set to 65° C. with shaking for 20 minutes. Slides were washed twice with double distilled water (DDW) for 5 minutes and were stripped from proteins by incubation with 20 µg/ml proteinase K (PK) (Roche Applied Science) for 15 minutes at room temperature, and then slides were washed in DDW for 2 minutes. TUNEL assay (Roche Applied Science) was performed according to the instructions by the manufacturer and stained with DAPI solution. At the end, slides were visualized by fluorescence microscopy (Nikon 50i, Kawasaki, Kanagawa, Japan).

Ki-67 is as large nuclear protein, preferentially expressed during all active parts of the cell cycle (G1, S and G2/M), but absent from resting cells (G0). Cell proliferation in the tumors was analyzed by immunohistochemistry with formalin fixed section stained with anti-rat Ki-67 antigen antibody (DakoCytomation), according to manufacturer instructions. Pretreatment of tissue sections was performed using PT system (Dako) using Target Retrieval Solution (Dako) at 97° C. for 20 minutes and then 60° C. for more 20 minutes. Slides were treated with peroxidase block (Envision FLEX Peroxidase-Blocking reagent, Dako) for 5 minutes, and rinsed with buffer for 5 minutes. Primary rat Ki-67 antibody was applied at 1:50 dilution for 30 minutes at room temperature. Then, slides rinsed twice for 5 minutes and secondary antibody (EmVision FLEX/HRP, Dako) was applied at 1:300 dilution. Slides were washed three times for 5 minutes in buffer and visualization was done using DAB+ (DakoCytomation) as chromagen and counterstained with hematoxylin.

In order to examine apoptotic characteristics in the tumors cells, the slides with tumor specimens were analyzed using TUNEL assay labeling and DAPI staining. DAPI staining of the slides of tumor specimens indicated that nuclear condensation, DNA fragmentation and prenuclear apoptotic bodies were induced by IV treatment. TUNEL assay labeling indicated presence of TUNEL positive cells (orange shining cells) showing that IV extract had induced apoptosis in the animal's cells (FIG. 37).

Cell proliferation in the tumors was examined using Ki-67 antibody. The number of proliferating cells (brown colored cells) in slides from the control was larger than in the slides from groups treated with 150 or 300 mg/kg IV, indicating that that IV extract decreases rate of cell proliferation in tumor cells (FIG. 38).

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method for treating colorectal cancer in a subject in need thereof, the method comprising the steps of:
   a) providing a pharmaceutical composition comprising a therapeutically effective amount of a water extract derived from *Dittrichia viscosa* leaves, wherein said leaves are harvested in the spring; and
   b) administering to the subject said pharmaceutical composition,
   thereby treating colorectal cancer in a subject.

2. The method of claim 1, wherein said *dittrichia viscosa* leaves are harvested prior to the blooming phase.

3. The method of claim 1, wherein the extract is administered in a dose of 8-80 mg/kg.

4. The method of claim 1, wherein the extract is administered in a dose of 12-24 mg/kg.

5. The method of claim 1, wherein the amount of the extract is from about 0.01% to about 99.9% (w/w) compared to the total weight of the composition, wherein said extract is in a liquid form.

6. The method of claim 4, wherein the amount of the extract is from about 0.01% to about 30% (w/w).

7. The method of claim 1, wherein said *dittrichia viscosa* are cultivated *dittrichia viscosa* plants.

8. The method of claim 1, wherein the pharmaceutical composition further comprises a pharmaceutically effective excipients, diluent and/or carrier.

9. The method of claim 1, wherein the composition is administered at least twice weekly.

10. The method of claim 1, wherein the composition is administered at least three times weekly.

11. The method of claim 1, wherein the composition is administered over at least 3 weeks.

12. The method of claim 1, wherein said administering is selected from intravenously, intratumorally, intraperitoneally or intramuscularly administration.

13. The method of claim 1, wherein said administering is intraperitoneally administration.

14. The method of claim 1, wherein the composition comprises at least one additional active agent.

* * * * *